US006909220B2

(12) United States Patent
Chen

(10) Patent No.: US 6,909,220 B2
(45) Date of Patent: Jun. 21, 2005

(54) HIGH STRAIN TEAR RESISTANT GELS AND GEL COMPOSITES FOR USE AS ARTIFICIAL MUSCLE ACTUATORS

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 15 days.

(21) Appl. No.: 10/273,828

(22) Filed: Oct. 17, 2002

(65) Prior Publication Data

US 2003/0122446 A1 Jul. 3, 2003

Related U.S. Application Data

(63) Continuation-in-part of application No. 09/517,230, filed on Mar. 2, 2000, now abandoned, and a continuation-in-part of application No. 09/412,886, filed on Oct. 5, 1999, now abandoned, and a continuation-in-part of application No. 09/285,809, filed on Apr. 1, 1999, now abandoned, and a continuation-in-part of application No. 09/274,498, filed on Mar. 28, 1999, now Pat. No. 6,420,475, and a continuation-in-part of application No. 09/130,545, filed on Aug. 8, 1998, now Pat. No. 6,627,275, and a continuation-in-part of application No. 08/984,459, filed on Dec. 3, 1997, now Pat. No. 6,324,703, and a continuation-in-part of application No. 08/909,487, filed on Jul. 12, 1997, now Pat. No. 6,050,781, and a continuation-in-part of application No. 08/863,794, filed on May 27, 1997, now Pat. No. 6,117,176, and a continuation-in-part of application No. PCT/US97/17534, filed on Sep. 30, 1997, and a continuation-in-part of application No. 08/719,817, filed on Sep. 30, 1996, now Pat. No. 6,148,830, and a continuation-in-part of application No. 08/665,343, filed on Jun. 17, 1996, which is a continuation-in-part of application No. 08/612,586, filed on Mar. 8, 1996, now Pat. No. 6,552,109, and a continuation-in-part of application No. PCT/US94/04278, filed on Apr. 19, 1994, and a continuation-in-part of application No. PCT/US94/07314, filed on Jun. 27, 1994.

(51) Int. Cl.[7] .............................................. H02N 01/00
(52) U.S. Cl. ........................ 310/309; 204/606; 204/607
(58) Field of Search ................................ 310/309, 306, 310/307, 363; 204/606, 607; 60/527, 528; 525/240, 250

(56) References Cited

U.S. PATENT DOCUMENTS

| 5,250,167 A | * | 10/1993 | Adolf et al. ................. 310/309 |
| 5,389,222 A | * | 2/1995 | Shahinpoor ................. 310/309 |
| 6,117,296 A | * | 9/2000 | Thomson .................... 204/607 |
| 6,249,076 B1 | * | 6/2001 | Madden et al. ............. 310/363 |

FOREIGN PATENT DOCUMENTS

| JP | 05-253175 | * 10/1993 | ............ A61B/1/00 |
| JP | 2000-253682 | * 9/2000 | ............ H02N/1/00 |

OTHER PUBLICATIONS

"Electrostatic Artificial Muscle: Compact, High Power, Linear Actuators with Multiple Layer Structures", Niino et al., Jan. 1994.*

Research of Artificial Muscles, SRI INT. www.iijnet.or.jp/MMC/no.14/act/11/sril.htm, Mar. 1, 2000.

Breakthroughs www.discover.com/aug_issue/breakbend-bots.html, Mar. 1, 2000.

Artificial Muscles www.sciam.com/explorations/05056explorationsbox4.html, Oct. 17, 2002.

From IV bags to bionic man www.engr.psu.edu/publications/EPS SPR99/zhang.html, Oct. 17, 2002.

* cited by examiner

Primary Examiner—Tamai IE Karl

(57) ABSTRACT

Novel gels and articles are formed from one or more copolymers having at least one poly(ethylene) components and high levels of one or more plasticizers, said gels having an amount of crystallinity, glassy components, and selected plasticizers sufficient to achieve improvements in one or more physical properties including improved crack propagation resistance, improved tear resistance, improved resistance to fatigue, resistance to catastrophic failure, and exhibiting high strain under elongations not obtainable in amorphous gels which high strain making the gel suitable for use as film layers for artificial muscles.

3 Claims, 5 Drawing Sheets

| M1 | Fabric |
|---|---|
| G | Gel |
| GM | Gel-Foam |
| M2 | Foam |
| M3 | Synthetic Resin or Plastic |
| M4 | Fibre |
| M5 | Concrete |
| M6 | Metal/Metal powder |
| M7 | Wood |
| M8 | Wire or Screening |
| M9 | Refractory Material |
| M10 | Other Material |
| M11 | Glass |

Figure 1

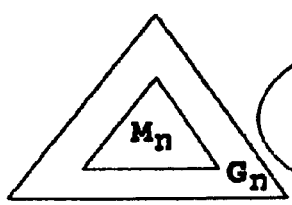 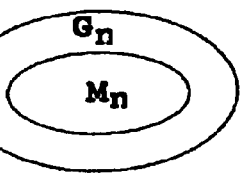 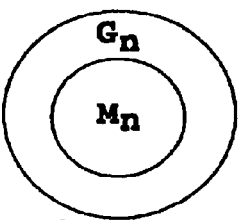 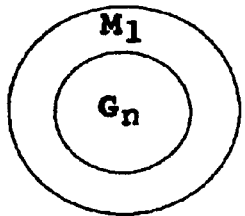
Figure 4a  Figure 4b  Figure 4c  Figure 4d
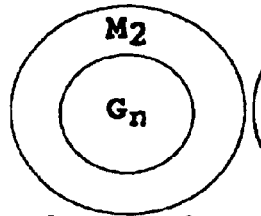 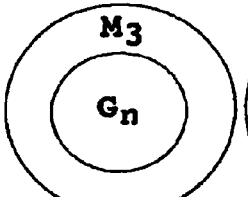 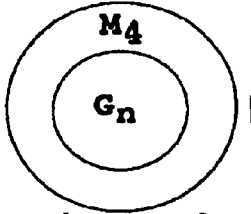 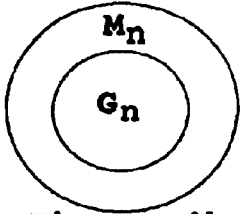
Figure 4e  Figure 4f  Figure 4g  Figure 4h
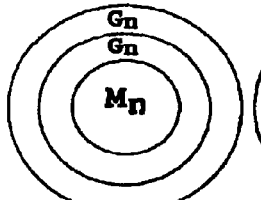 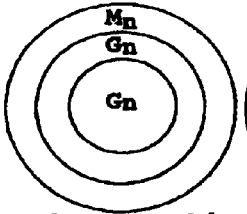 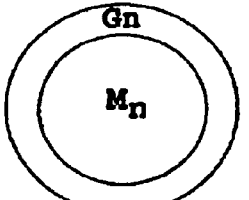 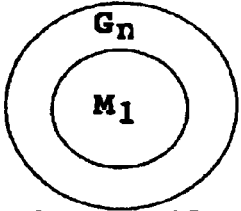
Figure 4i  Figure 4j  Figure 4k  Figure 4l
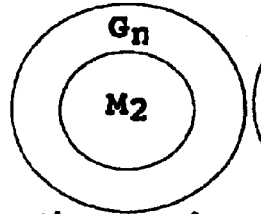 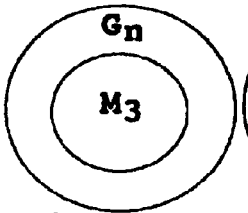 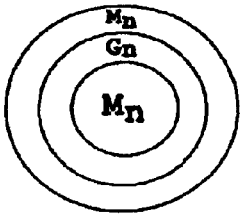 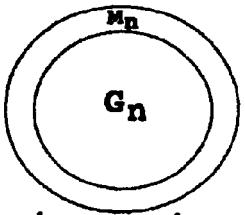
Figure 4m  Figure 4n  Figure 4o  Figure 4p
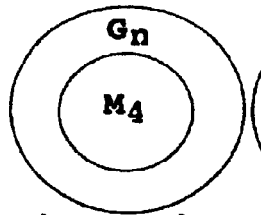 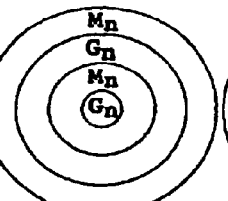 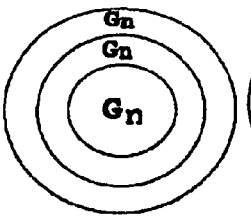 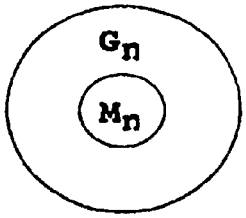
Figure 4q  Figure 4r  Figure 4s  Figure 4t
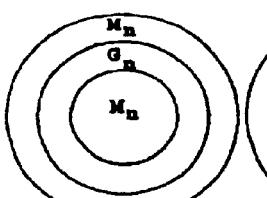 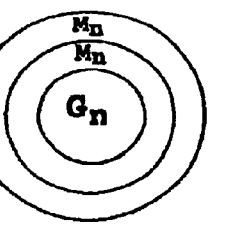 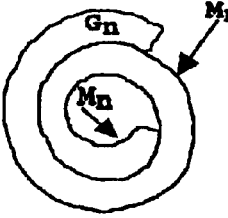 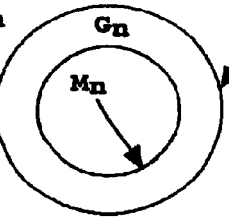
Figure 4u  Figure 4v  Figure 4w  Figure 4x

HIGH STRAIN TEAR RESISTANT GELS AND GEL COMPOSITES FOR USE AS ARTIFICIAL MUSCLE ACTUATORS

RELATED APPLICATIONS

This application is a continuation-in-part of the following application Ser. Nos. 09/517,230, filed Mar. 2, 2000, ABN Ser. No. 09/412,886, filed Oct. 5, 1999, ABN Ser. No. 09/285,809, filed Apr. 1, 1999 ABN now U.S. Pat. No. 6,050,781 Ser. No. 09/274,498, filed Mar. 28, 1999; now U.S. Pat. No. 6,420,475 Ser. No. 09/130,545, filed Aug. 8, 1998, now U.S. Pat No. 6,627,275 Ser. No. 80/984,459, filed Dec. 3, 1997 Ser. No. 08/909,487, now U.S. Pat. No. 6,324,703 filed Aug. 12, 1997, Ser. No. 08/863,794, filed May 27, 1997: now U.S. Pat. No. 6,117,176 PCT/US97/17534, filed Sep. 30, 1997, U.S. Ser. No. 08/719,817 filed Sep. 30, 1996, now U.S. Pat. No. 6,148,130 U.S. Ser. No. 08/665,343 filed Jun. 17, 1996 which is a Continuation-in-part of U.S. Ser. No. 08/612,586 filed Mar. 8, 1996, U.S. Pat No. 6,562,109 PCT/US94/04278 filed Apr. 19, 1994 (published May 26, 1995 No. WO95/13851); PCT/US94/07314 filed Jun. 27, 1994 (published Jan. 4, 1996 No. WO 96/00118), Ser. No. 08/288,690 filed Aug. 11, 1994, U.S. Pat No. 5,633,286 Ser. No. 08/581,188 filed Dec. 29, 1995, ABN Ser. No. 08/581,191 filed Dec. 29, 1995 U.S. Pat. No. 5,766,117, Ser. No. 08/581,125 filed Dec. 29, 1995 now U.S. Pat. No. 5,962,572. In turn U.S. Ser. Nos. 08/581,188; 08/581,191, and 08/581,125 (now U.S. Pat. No. 5,962,572) are continuation-in-parts of the following applications Ser. Nos. 08/288,690, filed Aug. 11, 1994, PCT/US94/07314 filed Jun. 27, 1994 (CIP of PCT/US 94/04278, filed Apr. 19, 1994) The subject matter contained in the related applications and patents are specifically incorporated herein by reference

FIELD OF THE INVENTION

The present invention is directed to novel gels, composites and articles as artificial muscles

BACKGROUND OF THE INVENTION

There have been many breakthroughs published on the internet including muscles made from flexible polymer ribbons constructed from chains of carbon, fluorine, and oxygen molecules (Yoseph Bar-Cohen@ www discover com/augustissue/breakbend bots html) Mo Shahinpoor makes his out of polyacrylonitrile, see www sciam com/explorations/050596explorationsbox4 html, and a polymer muscle consists of thin sheets wrapped into a cigarlike cylinder Other types of (internet announced) polymer muscle are thin sheets wrapped into a cigarlike cylinder These polymers stretch when one side of a sheet is given a positive charge and the other a negative These charges cause each wrapped sheet to contract toward the center of the cylinder, and this construction forces the cylinder to expand lengthwise When the power supply is off, the rope relaxes These polymers can push, pull, and lift loads SRI International is investigating artificial muscle for small robots using electrostrictive polymers The muscle has compliant electrodes on the surface of the polymer film, contracts in thickness and extends in length and width due to the electrostatic forces when a voltage is applied The polymer enhances the electrostatic force because of its dielectric constant The net result is a muscle with a large strain (>30%) and a large actuation pressure (0.21 MPa in silicon, 1.9 MPa in polyurethane) The performance of the artificial muscle is comparable to the natural muscle, but with higher efficiency and faster response Artificial muscle can be fabricated using spin coating, dipping, or casting Once the muscle is fabricated, it can also be folded or rolled to make the muscle actuator more compact The artificial muscle actuator shown in FIG. 2 uses a spin coated film which is first folded then rolled, followed by folding and to achieve 20 layers The active muscle for the actuator is 10 mm in length and 3 mm in diameter, and gives a maximum stroke of 1 mm and maximum force of 2 grams ($2\times10^4$ uN) Its weight is approximately 0.1 grams The ability to reduce the number of layers and increase the muscle material's strain, thereby greatly reducing the size of the active muscle actuator and/or increasing the stroke distance at a greater force are challenges not achieved in the prior art This application is based upon subject matters described in earlier filed and copending related applications and patents (see Related Applications above) which are specifically incorporated herein by reference

SUMMARY OF THE INVENTION

I have now discovered novel gels with improved properties made from thermoplastic elastomer random copolymers and block copolymers having one or more polyethylene segment midblocks exhibiting greater advantage over other non-ethylene component forming gels for making artificial muscles. The gels advantageously exhibit high tear resistances, high tensile strength and exhibit high strain under elongation. Such gels are advantageous for end-use involving repeated applications of stress and strain resulting from large number of cycles of elongations, deformations, including compression, compression-extension (elongation), torsion, torsion-compression, torsion-elongation, tension, tension-compression, tension-torsion, exhibit high strain under elongation and the like. The gels also exhibit improved damage tolerance, crack propagation resistance and especially improved resistance to high stress rupture which combination of properties makes the gels advantageously and surprisingly exceptionally more suitable for use as artificial muscles than amorphous gels made from non-poly(ethylene) component copolymers at corresponding gel Bloom rigidities.

The artificial muscle actuators of the invention comprises one or more thin film layers folded or rolled into the shape of a cylinder forming a center part of said cylinder and an outer part of said cylinder, said film layer having a top surface and a bottom surface, said top surface and said bottom surface each coated with an electrical conducting layer, said conducting layer of said top surface connected by a first electrode on said top surface positioned at said center part and said bottom surface connected by a second electrode on said bottom surface positioned at said outer part; said first and second electrodes being connected to a direct current power source, said power supply capable of generating a electrical potential of a positive electrical charge to the first electrode and a negative electrical charge to the second electrode of at least about 10,000 volts; said film layers comprising a gel made from one or more copolymers characterized by sufficient crystallinity as to exhibit a melting endotherm of at least about 25° C. as determined by DSC curve, and said gel being characterized by sufficient crystallinity as to exhibit a melting endotherm of about 25° C., 21° C., 22° C., 23° C., 24° C., 25° C., 26° C., 27° C., 28° C., 29° C., 30° C., 31° C., 32° C., 33° C., 34° C., 35° C., 36°

C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C. or higher as determined by differential scanning calorimeter (DSC) curve, said gel having rigidities of from less than about 2 gram Bloom to about 1,800 gram Bloom; and said gel having sufficient crystallinity so as to exhibit greater strain under elongation than amorphous gels of SEPS and SEBS.

The usefulness of the gels as artificial muscles is because of the inherent crystallinity of one or more components of the copolymers forming the gels which makes the gels useful as artificial muscles. The crystallinity provides greater strain under elongation which advantage is surprisingly not found in gels of corresponding gel rigidities made from amorphous block copolymers such as poly(styrene-ethylene-butylene-styrene), poly(styrene-ethylene-propylene-styrene), high vinyl poly(styrene-ethylene-butylene-styrene), poly(styrene-ethylene-ethylene-butylene-styrene) alone.

As used herein, the term "gel rigidity" in gram Bloom is determined by the gram weight required to depress a gel a distance of 4 mm with a piston having a cross-sectional area of 1 square centimeter at 23° C.

The various aspects and advantages will become apparent to those skilled in the art upon consideration of the accompanying disclosure.

DESCRIPTION OF THE DRAWINGS

FIG. 1. Representative sectional view of gel, composite and gel articles useful as artificial muscles.

FIGS. 4a–4x. Representative sectional view of gel, composite and gel articles useful as artificial muscles.

DESCRIPTION OF THE INVENTION

Figure 2A:
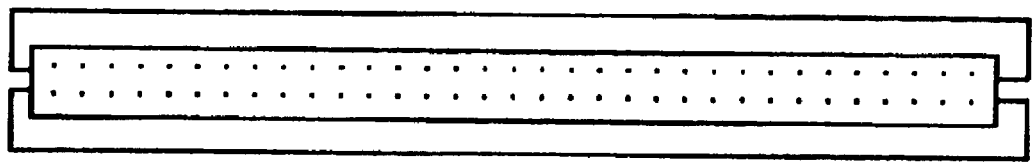
FIGS. 2A–2d. Representative sectional view of gel, composite and gel articles useful as artificial muscles.

Thermoplastic elastomer gels are described in my patents and published applications: PCT/US97/17534; PCT/US94/04278; PCT/US94/07314; U.S. Pat. Nos. 5,884,639; 5,868,597; 5,760,117; 5,655,947; 5,624,294; 5,508,334; 5,475,890; 5,336,708; 5,324,222; 5,262,468; 5,239,723; 5,153,254; 4,618,213; and 4,369,284. Various patents on thermoplastic elastomers and blends are described in U.S. Pat. Nos. 5,755,243; 3,595,942, Reissue 27,145-28,236; 3,772,234; 4,116,917; 4,687,815; and 4,880,878. Other non-patent publications related to S-EB-S polymers include (1) W. P. Gergen, "Uniqueness of Hydrogenated Block Copolymers for Elastomeric Applications," presented at the German Rubber Meeting, Wiesbaden, 1983, Kautsch, Gummi, Kunstst. 37, 284 (1984). (2) W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". (3) L. Zotteri and et al., "Effect of hydrogenation on the elastic properties of poly(styrene-b-diene-b-styrene) copolymers", Polymer, 1978, Vol. 19, April. (4) J. Kenneth Craver, et al., Applied Polymer Science, Ch. 29, "Chemistry and Technology of Block Polymers", pp 394–429, 1975. (5) Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G-0201. (6) J E. McGrath, et al., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. (7) Legge, Norman R., "Thermoplastic Elastomers", Charles Goodyear Medal address given at the 131st Meeting of the Rubber Division, American Chemical Society, Montreal, Quebec, Canada, Vol. 60, G79-G115, May 26–29, 1987. (8) Falk, John Carl, and et al., "Synthesis and Properties of Ethylene-Butylene-1 Block Copolymers", Macromolecules, Vol. 4, No. 2, pp. 152–154, March–April 1971. (9) Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. (10) Yee, A. F, and et al., "Modification of PS by S-EB-S Block Copolymers: Effect of Block Length", General Electric Corporate Research & Development, Schenectady, N.Y. 12301. (11) Siegfried, D. L., and et al, "Thermoplastic Interpenetrating Polymer Networks of a Triblock Copolymer elastomer and an Ionomeric Plastic Mechanical Behavior", Polymer Engineering and Science, January 1981, Vol. 21, No.1, pp 39–46. (12) Clair, D. J., "S-EB-S Copolymers Exhibit Improve Wax Compatibility", Adhesives Age, November, 1988. (13) Shell Chemical Technical Bulletin SC: 1102–89, "Kraton® Thermoplast Rubbers in oil gels", April 1989 (14) Chung P. Park and George P. Clingerman, "Compatibilization of Polyethylene-Polystyrene Blends with Ethylene-Styrene Random Copolymers", the Dow Chemical Company, May 1996. (15) Steve Hoenig, Bob Turley and Bill Van Volkenburgh, "Material Properties and Applications of Ethylene-Styrene Interpolymers", the Dow Chemical Company, September 1996. (16) Y. Wilson Cheung and Martin J. Guest, "Structure, Thermal Transitions and Mechanical Properties of Ethylene/Styrene Copolymers", the Dow Chemical Company, May 1996. (17) Teresa Plumley Karjaia, Y. Wilson Cheung and Martin J. Guest, "Melt Rheology and Processability of Ethylene/Styrene Interpolymers", the Dow Chemical Company, May 1997. (18) D. C. Prevorsek, et al., "Origins of Damage Tolerance in Ultrastrong Polyethylene Fibers and Composites:, Journal of Polymer Science: Polymer Symposia No. 75, 81–104 (1993). (19) Chen, H., et al, "Classification of Ethylene-Styrene Interpolymers Based on Comonomer Content", J. Appl. Polym. Sci., 1998, 70, 109. (20–24) U.S. Pat. Nos. 5,872,201; 5,460,818; 5,244,996; EP 415815A; JP07,278, 230 describes substantially random, more appropriately presudo-random copolymers (interpolymers), methods of making and their uses. (25) Alizadeh, et al., "Effect of Topological Constraints on The Crystallization Behavior of Ethylene/alp[ha-Olefin Copolymers", PMSE, Vol, 81, pp. 248–249, Aug. 22–26, 1999. (26) Guest et al., "Structure/Property Relationships of Semi-Crystalline Ethylene-Styrene Interpolymers (ESI)", PMSE, Vol, 81, pp. 371–372, Aug. 22–26, 1999. The above applications, patents and publications are specifically incorporated herein by reference.

Legge's paper teaches the development of (conventional substantially amorphous elastomer midsegment) SEBS triblock copolymers. In the polymerization of butadiene by alkylithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer midsegment. Using a mixture of 1,4- and 1,2-polybutadiene as the base polymer for the midsegment would result in an ethylene/butylene midsegment in the final product. The elements of selection of the midsegment composition is elastomer crystallinity and the elastomer Tg of an ethylene/butylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers.

Clair's paper teaches that the EB midblock of conventional S-EB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DSC) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the ethylene midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves of these polymers. The maximum in this broad endotherm occurs at about 40° C.

Himes, et al., (U.S. Pat. No. 4,880,878) describes SEBS blends with improved resistance to oil absorption.

Papers (14)–(17) describes poly(ethylene-styrene) substantially random copolymers (Dow Interpolymers™): Dow S, M and E Series produced by metallocene catalysts, using single site, constrained geometry addition polymerization catalysts resulting in poly(ethylene-styrene) substantially random copolymers with weight average molecular weight (Mw) typically in the range of $1 \times 10^5$ to $4 \times 10^5$, and molecular weight distributions (Mw/Mn) in the range of 2 to 5.

Paper (18) Prevorsek, et al., using Raman spectroscopy, WAXS, SAXD, and EM analysis interprets damage tolerance of ultrastrong PE fibers attributed to the nano scale composite structure that consists of needle-like-nearly perfect crystals that are covalently bonded to a rubbery matrix with a structure remarkably similar to the structure of NACRE of abalone shells which explains the damage tolerance and impact resistance of PE fibers. PE because of its unique small repeating unit, chain flexibility, ability to undergo solid state transformation of the polyethylene phase without breaking primary bonds, and its low glass transition temperature which are responsible for large strain rate effects plays a key role in the damage tolerance and fatigue resistance of structures made of PE fibers.

Figure 2B:
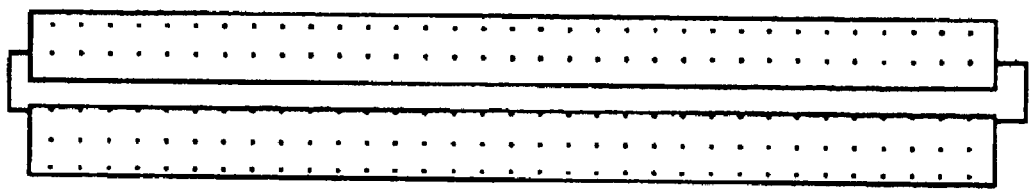
Figure 2C:
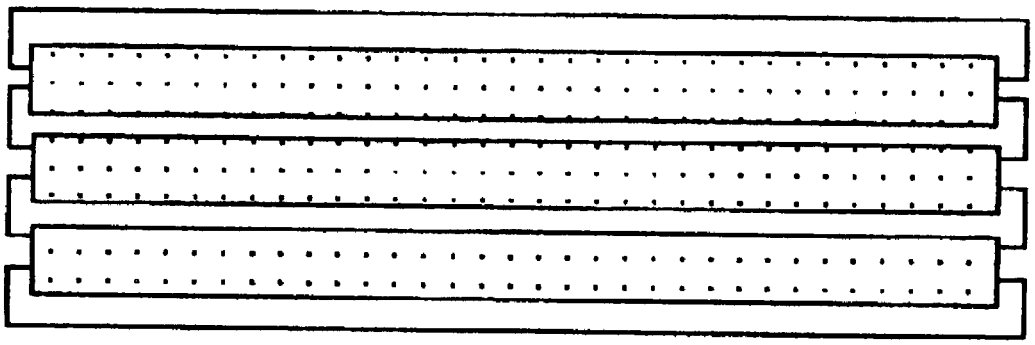
Figure 2D:
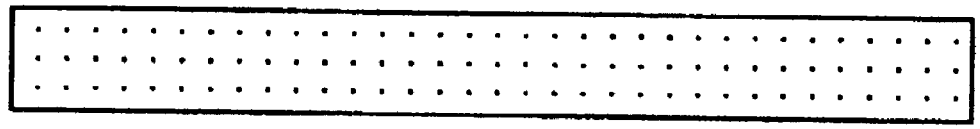
Figure 3A:
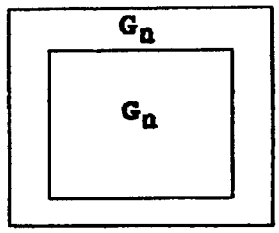
FIGS. 3A–3n. Representative sectional view of gel, composite and gel articles useful as artificial muscles.
Figure 3B:
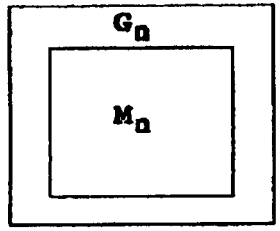
Figure 3C:
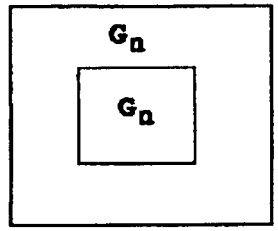
Figure 3D:
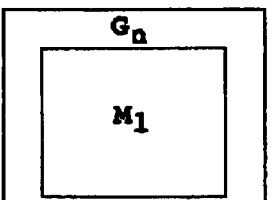
Figure 3E:
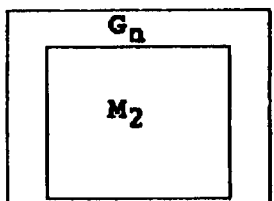
Figure 3F:
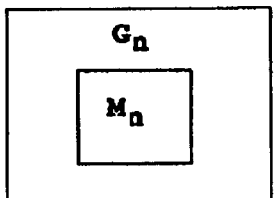
Figure 3G:
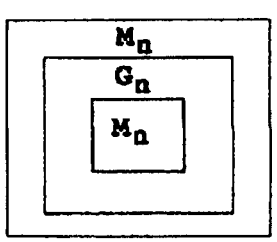
Figure 3H:
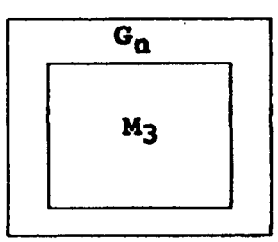
Figure 3I:
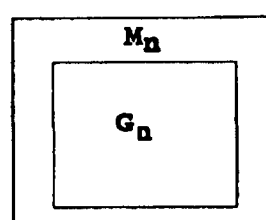
Figure 3J:
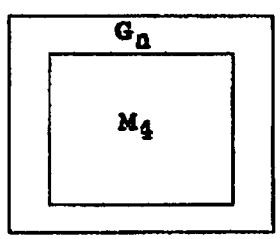
Figure 3K:
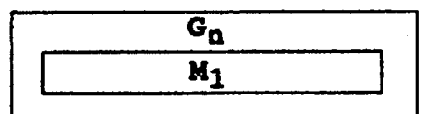
Figure 3L:
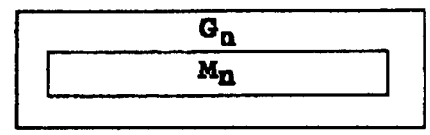
Figure 3M:
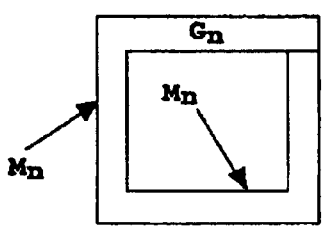
Figure 3N:
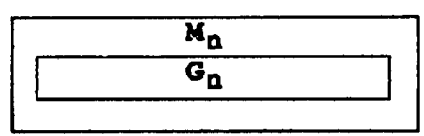
Figure 5:
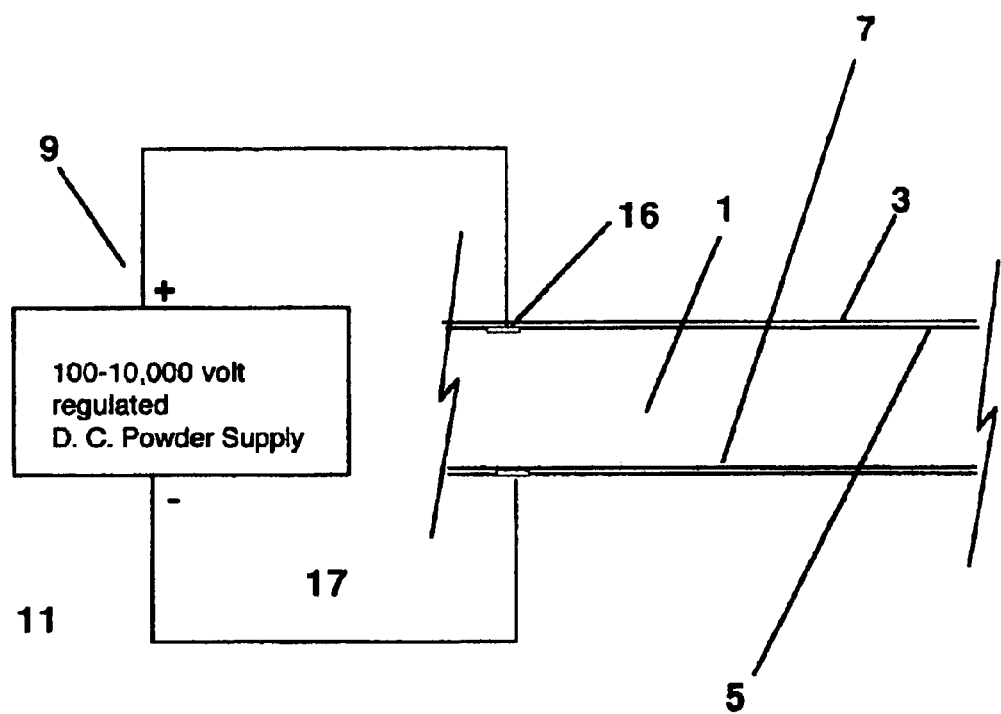
FIG. 5. Representative sectional view of the electrodes and gel in an artificial muscle.

Chen (19) classifies 3 distinct categories of E (approximately 20–50 wt % styrene), M (approximately 50–70 wt % styrene), & S (greater than approximately 70 wt % styrene) substantially random or more appropriately pseudo-random ethylene-styrene copolymers or random copolymers of ethylene and ethylene-styrene dyads. The designated Ethylene-styrene copolymers are: E copolymers (ES16, ES24, ES27, ES28, ES30, and ES44 with styrene wt % of 15.7, 23.7, 27.3, 28.1, 39.6 & 43.9 respectively), M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively), S copolymers (ES72, ES73, and ES74 with styrene wt % of 72.7, 72.8, and 74.3 respectively). The maximum comonomer content for crystallization of about 20% is similar in other ethylene copolymers, such as in ethylene-hexene and ethylene-vinyl acetate copolymers. If the comonomer can enter the crystal lattice, such as in ethylene-propylene, compositions in excess of 20 mol % comonomer can exhibit crystallinity. The molecular weight distribution of these copolymers is narrow, and the comonomer distribution is homogeneous. These copolymers exhibit high ethylene, lamellar morphologies to fringed micellar morphologies of low crystallinity. Crystallinity is determined by DSC measurements using a Rheometric DSC. Specimens weighing between 5 and 10 mg are heated from −80 to 180° C. at a rate of 10° C./min (first heating), held at 190° C. for 3 min, cooled to −80° C. at 10° C./min, held at −80° C. for 3 min,and reheated from −80° C. to 180° C. at 10° C./min (second heating). The crystallinity (wt %) is calculated from the second heating using a heat of fusion of 290 J/g for the polyethylene. Contributing effects of the crystallinity include decrease volume fraction of the amorphous phase, restricted mobility of the amorphous chain segments by the ethylene domains, and higher styrene content of the amorphous phase due to segregation of styrene into the amorphous phase. Table I of this paper shows values of Total Styrene (wt %), aPS (wt %), Styrene (wt %), Styrene (mol %), $10^{-3}$ Mw, Mw/Mn, and Talc (wt %) for Ethylene-styrene copolymers ES16–ES74 while FIGS. 1–12 of this paper shows: (1) melting thermograms of ESI 1st and 2nd heating for ES16, ES27, ES44, ES53, ES63, & ES74; (2) crystallinity from DSC as a function of conmonomer content; (3) Logarithmic plot of the DSC heat of melting vs. Mole % ethylene for ESIs; (4) measured density as a function of styrene content for semi-crystalline and amorphous ESIs; (5) % crystallinity from density vs % crystallinity from DSC melting enthalpy; (6) Dynamic mechanical relaxation behavior; (7) Glass transition temperature as a function of wt % ethylene-styrene dyads for semicrystalline and amorphous ESIs, (8) Arrhenius plots of the loss tangent peak temperature for representative semicrystalline and amorphous ESIs; (9) Draw ratio vs engineering strain; (10) Engineering stress-strain curves at 3 strain rates for ES27, ES63 and ES74; (11) Engineering stress-strain curves of ESIs; (12) Classification scheme of ESIs based on composition.

(20) U.S. Pat. No. 5,872,201 describes interpolymers, terpolymers of ethylene/styrene/propylene, ethylene/styrene/4-methyl-1-pentene, ethylene/styrene/hexend-1, ethylene/styrene/octene-1, and ethylene/styrene/norbornene with number average molecular weight (Mn) of from 1,000 to 500,000.

(21–24) U.S. Pat. Nos. 5,460,818; 5,244,996; EP 41 5815A; JP07,278,230 describes substantially random, more appropriately presudo-random copolymers (interpolymers), methods of making and their uses.

(25) Alizadeh, et al., find the styrene interpolymers impedes the crystallization of shorter ethylene crystallizable sequences and that two distinct morphological features (lamellae and fringe micellar or clain clusters) are observed in ethylene/styrene (3.4 mol %) as lamella crystals organized in stacks coexisting with interlamellar bridge-like structures.

(26) Guest, et al., describes ethylene-styrene copolymers having less than about 45 wt % copolymer styrene being semicrystalline, as evidenced by a melting endotherm in DSC testing (Dupont DSC-901, 10° C./min) data from the second heating curve. Crystallization decreases with increasing styrene content Based on steric hindrance, styrene unit is excluded from the ethylene region of the copolymers. Transition from ethylene to amorphous solid-state occurs at about 45 to 50 wt % styrene. At low styrene contents (<40%), the copolymers exhibit a relatively well-defined melting process. FIGS. 1–5 of this paper shows (a) DSC data in the T range associated with the melting transition for a range of ESI differing primarily in copolymer styrene content, (b) variation in percent crystallinity (DSC) for ESI as a function of copolymer S content, (c) elastic modulus versus T for selected ESI differing in S content, (d) loss modulus versus T for selected ESI differing in S content, (e) Tensile stress/strain behavior of ESI differing in S content, respectively. The above patents and publications are specifically incorporated herein by reference.

Prior amorphous gels made from SEPS and SEBS are inadequate for the most demanding applications involving endurance at high stress and strain levels over an extended period of time exhibiting greater strain under elongation which are essential for the gels to have uses as artificial muscles.

The gels which are advantageously useful for making artificial muscles, toys, medical devices, and other useful articles of manufacture including disposable inflatable restraint cushions, and especially for use as artificial muscles, and the like. Said gels comprises: 100 parts by weight of one or more high viscosity (I) linear triblock copolymers, (II) multi-arm block copolymers, (III) branched block copolymers, (IV) radial block copolymers, (V) multiblock copolymers, (VI) random copolymers, (VII) thermoplastic crystalline polyurethane copolymers with hydrocarbon midblocks or mixtures of two or more (I)–(VII) copolymers in combination with or without major or minor amounts of one or more other (VIII) copolymers or polymers, said copolymers having one or more segments or one or more midblocks comprising one or more polyethylene segments or midblocks and selected amounts of a compatible plasticizer (IX) sufficient to achieve gel rigidities of from less than about 2 gram Bloom to about 1,800 gram Bloom and higher with the proviso that when said (I)–(VII) copolymers having nil amorphous segment or nil amorphous midblock are combined with one or more (VIII) copolymers having one or more amorphous segments or amorphous midblocks to form a stable plasticizer compatible gel.

With respect to the random copolymers (VI) embodiments forming the gels of the invention, such gels comprises:

(i) one or more substantially random copolymers (pseudo-random copolymers or interpolymers) having one or more glassy components and at least one substantially ethylene components, wherein said (i) copolymers being in combination with a selected amount of one or more selected second copolymers comprising:

(ii) one or more substantially random copolymers having one or more glassy components and one or more ethylene components of moderate crystallinity;

(iii) one or more substantially random copolymers having one or more glassy components and one or more ethylene components of low crystallinity;

(iv) one or more substantially random copolymers having one or more glassy components and one or more amorphous components;

(v) one or more of a diblock, triblock, multi-arm block, branched block, radial block, or multiblock copolymers, wherein said (v) copolymers having one or more glassy components and one or more elastomeric components of selected crystallinity; and (vi) one or more of a diblock, triblock, multi-arm block, branched block, radial block, or multiblock copolymers, wherein said (vi) copolymers having one or more glassy components and one or more amorphous elastomeric components;

(vii) a mixture of two or more (ii)–(vi) copolymers; wherein said (i)–(iii) and (v) copolymers are characterized by sufficient crystallinity as to exhibit a melting endotherm of at least about 25° C. as determined by DSC curve, and said gel being characterized by sufficient crystallinity as to exhibit a melting endotherm of at least about 10° C. as determined by DSC curve;

(II) in combination with or without one or more of selected homopolymers; and (III) a selected amount of one or more compatible plasticizers of sufficient amounts to achieve a stable gel having rigidities of from less than about 2 gram Bloom to about 1,800 gram Bloom.

The gels comprising the thermoplastic elastomer copolymers and block copolymers having one or more polyethylene segments or midblocks of the invention are hereafter referred to as "elastic gels" or simpler "gels". The crystalline copolymers are characterized by sufficient crystallinity as to exhibit a melting endotherm of at least about 25° C. as determined by DSC curve, and said gel being characterized by sufficient crystallinity as to exhibit a melting endotherm of at least about 10° C. as determined by DSC curve.

The various types of copolymers and block copolymers employed in forming the crystal-gels of the invention are of the general configurations (Y-AY)$_n$ copolymers, A-Z-A, and (A-Z)n block copolymers, wherein the subscript n is a number of two or greater. In the case of multiarm block copolymers where n is 2, the block copolymer denoted by (A-Z)n is A-Z-A. It is understood that the coupling agent is ignored for sake of simplicity in the description of the (A-Z)n block copolymers.

The segment (A) comprises a glassy amorphous polymer end block segment which can be polystyrene, poly(alpha-methylstyrene), poly(o-methylstyrene), poly(m-methylstryene), poly(p-methylstyrene) and the like, preferably, polystyrene.

The segment (Y) of copolymers (Y-AY)$_n$ comprises poly(ethylene) (simply denoted by "-E-" or (E)). In the case of copolymers (A-Y)$_n$, (Y) when next to (A) may be substantially non-ethylene or amorphous ethylene segments. For example a polyethylene copolymer (Y-AY)$_n$ may be represented by: . . . -E-E-E-E-E-E-E-E-SE-E-E-E-E-E-SE-E-E-E-E-E-SE- . . . . Where Y is a long run of polyethylene or a non-ethylene copolymer (AY-AY)$_n$ . . . -E-SE-SE-E-SE-E-SE-E-SE-E-E-SE-SE-E-SE- . . . where Y is a non-polyethylene run of ethylene.

Other substantially random copolymers suitable for forming gels of the invention include (Y-A-Y') where Y is a polyethylene run of ethylene and Y' can be propylene, 4-methyl-1-pentene, hexene-1, octene-1, and norborene. A can be styrene, vinyl toluene, alpha-methylstyrene, t-butylstyrene, chlorostyrene, including isomers and the like. Examples are: poly(ethylene-styrene) (ES), poly(ethylene-styrene-propylene) (ESP), poly(ethylene-styrene-4-methyl-1-pentene) (ES4M1P), poly(ethylene-styrene-hexend-1) (ESH1), poly(ethylene-styrene-octene-1) (ESO1), and poly(ethylene-styrene-norborene) (ESN), poly(ethylene-alpha-methylstyrene-propylene), poly(ethylene-alpha-methylstyrene-4-methyl-1-pentene), poly(ethylene-alpha-methylstyrene-hexend-1), poly(ethylene-alpha-methylstyrene-octene-1), and poly(ethylene-alpha-methylstyrene-norborene) and the like.

The end block segment (A) comprises a glassy amorphous polymer end block segment which can be polystyrene, poly(alpha-methylstyrene), poly(o-methylstyrene), poly(m-methylstryene), poly(p-methylstyrene) and the like, preferably, polystyrene. The segment (Y) of random copolymers A-Y comprises poly(ethylene) (simply denoted by "-E-" or (E)). In the case of random copolymers A-Y, (Y) may be substantially non-ethylene or amorphous ethylene segments. The midblocks (Z) comprises one or more midblocks of poly(ethylene) (simply denoted by "-E- or (E)") with or without one or more amorphous midblocks of poly(butylene), poly(ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z, and A and Y portions are incompatible and form a two or more-phase system consisting of sub-micron amorphous glassy domains (A) interconnected by (Z) or (Y) chains. The glassy domains serve to crosslink and reinforce the structure. The number average molecular weight (Mn) of the random copolymers is preferably greater than 1,000, advantageously from about 5,000 to about 1,100,000, more advantageously from abut 8,000 to about 700,000. Examples are:

The method of making Y-A-Y and Y-A-Y' random copolymers by metallocene single site catalysts are described in U.S. Pat. Nos. 5,871,201, 5,470,993, 5,055,438, 5,057,475, 5,096,867, 5,064,802, 5,132,380. 5,189,192, 5,321,106, 5,347,024, 5,350,723, 5,374,696, 5,399,635, and 5,556,928, 5,244,996, application EP A-0416815, EP-A-514828, EP-A-520732, WO 94/00500 all of which disclosure are incorporated herein by reference.

The linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The poly(ethylene/styrene) copolymers, type S series has more than 50 wt % styrene and is glassy at short times and rubbery at long times and exhibits ambient Tg, melt density of about higher than 0.952 to about 0.929 and less, typical Mw=about less than 150,000 to 350,000 and higher.

The type M series has more than 50 wt % styrene is amorphous rubber and exhibits very low modulus, high elasticity, low Tg of from greater than 10° C. to less than −50° C., melt Index of from higher than 5 to less than about 0.1, melt density of higher than 0.93 to 9.0 and less, typical Mw=about less than 200,000 to 300,000 and higher.

The type E series contains up to 50 wt % styrene is semi-crystalline rubber and exhibits low Tg of from greater than 0° C. to about less than −70, low modulus semi-crystalline, good compression set, Melt Index of from about higher than 2 to less than 0.03, melt density of about higher than 0.90 to 0.805 and less, Mw=about less than 250,000 to 350,000 and higher.

The E series random copolymers can be blended with the type M and type S series copolymers (having high glassy components) and one or more of the i, ii, iii, iv, v, vii and viii copolymers, plasticizers to form crystalline polymer Gels of the invention.

This physical elastomeric network structure is reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) or (A) and (Y) phases (mesophases) can take the form of spheres, cylinders, lamellae, or bicontinous structures. The scale of separation of the phases are typically of the order of hundreds of angstroms, depending upon molecular weights (i.e. Radii of gyration) of the minority-component segments. At such small domain scales, when the gel is in the molten state while heated and brought into contact to be formed with any substrate and allowed to cool, the glassy domains of the gel become interlocked with the surface of the substrate. At sufficiently high enough temperatures, with or without the aid of other glassy resins, the glassy domains of the copolymers forming the gels fusses and interlocks with even a visibly smooth substrate surface such as glass. The disruption of the sub-micron domains due to heating above the softening point forces the glassy domains to open up, unlocking the network structure and flow. Upon cooling below the softing point the glassy polymers reforms together into sub-micron domains, locking into a network structure once again, resisting flow. It is this unlocking and locking of the network structure on the sub-micron scale with the surfaces of various materials which allows the gel to form interlocking composites with other materials. Such interlocking with many different materials produce gel composites having many uses.

The (I) linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The (II, IV, and V) branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The gels can be made in combination with a selected amount of one or more selected polymers and copolymers (II) including thermoplastic crystalline polyurethane elastomers with hydrocarbon blocks, homopolymers, copolymers, block copolymers, polyethylene copolymers, polypropylene copolymers, and the like described below.

The gels of the invention are also suitable in physically interlocking or forming with other selected materials to form composites combinations. The materials are selected from the group consisting of paper, foam, plastic, fabric, metal, metal foil, concrete, wood, glass, various natural and synthetic fibers, including glass fibers, ceramics, synthetic resin, and refractory materials.

The high tear resistant soft gels are advantageously suitable for a safer impact deployable air bag cushions, the higher tear resistant gels are advantageously more suitable, and the highest tear resistant gels are advantageously even more suitable for such use and other uses. As impact deployable air bag cushions under expansion exhibit greater strain, the greater strain property makes also a better artificial muscle.

Very thin films of the gels of the invention are suitable for use as artificial muscles in the form of thin films wrapped Into a cylinder. The gel (1) film stretch when one side of a film is given a positive charge and the other a negative. The charges cause each wrapped film to contract toward the center of the cylinder which forces the cylinder to expand lengthwise, When the power supply is off, the cylindrical muscles relaxes. Thus, the roll up gel can push, pull, and lift loads.

A thin films or membrane of the gels having a thickness of about 5 mm to less than 0.1 mm are useful as artificial muscles. Film thickness of from 0.005 mm, 0.01 mm, 0.02 mm, 0.03 mm, 0.04 mm, 0.05 mm, 0.06 mm, 0.07 mm, 0.08 mm, 0.09 mm, 0.10 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm , 4.0 mm can be utilized for forming artificial muscles of the invention.

Fine powder of the common transition metals (3) can be utilized as a coating electrode(s) on the top surfaces $M_{n1}$ (5) and bottom surfaces $M_{n2}$ (7) comprising the two (flat) sides of the gel films to serve as conductor(s) $M_C$, such as aluminum, alpha aluminum, copper, silver, gold, tin, nickel, iron, cobalt, zinc, lead, and the like.

We denote "|" as a gel film layer, G, and "||" as two gel film layers, GG, side by side, "|||" as three gel film layers, GGG, side by side. We denote E as a metal electrode or conductor electrode on both sides of the G film layer, such as EGE, EGEGE, EGEGEGE, EGEGEGEGE and the like. We denote (+) as a positive charge, (−) as a negative charge. We then denote the single charged membrane or film layer as "(+)E|E(−)" showing a single gel layer with electrodes on both sides and a positive charge on its left side and a negative charge on its right side. Hence "(+)E|E(−)(−)E|E (+)", denotes a double gel thin film layers with electrodes on each side of the film layers and charged from left to right as positive (9), negative (11), negative, and positive. This arrangement allows for the rolling up of the double layers into a cylindrical cylinder (FIG. 4w) without discharging the double layers by rolling unto itself. Another way of rolling up a thin gel film "(+)E|E(−)" require folding the (−) side with the (−) sides as a continuous S curve layers upon layers and then rolling the S curve so that the same charged sides roll unto itself into a cylinder. Other combination can be made for use as charged thin film layers for artificial muscle use, such as a) (+)E|E(−),
b) (+)E|E(−)(−)E|E(+),
c) (+)E|E(−)(−)E|E(+)(+)E|E (−),
d) (+)E|E (−)(−)E|E(+)(+)E|E(−) (−)E|E(+), and
e) (+)E|E(−)(−)E|E(+)(+)E|E(−)(−)E|E(+)(+)E|E (−).

Moreover, the gels films can be formed as composite multiple layers of films with separating electrical conducting layer(s) with encapsulated connectors for easy folding.

The diameter of the rolled up gel cylinder can be from abQut 1 mm to abut 8 mm, suitably, about 0.5 mm to about 5 mm, more suitably about 1 mm to about 3 mm. Generally the rolled up diameter can be from less than 0.5 mm to about 12 mm or larger. The length of the cylinder can be almost any suitable length, from about 5 mm to about 50 mm, suitably, 8 mm to 20 mm, more suitably from less than 8 mm to 12 mm and longer.

Conductive connectors (of foil, polymer, or conductive gel) (16) can be attached to the corresponding inner and outer electrodes respectively. The direct current voltage from a regulated power supply (17) or predetermined voltage positive or negative potential source can be applied to the corresponding inner and outer electrodes in contact with the gel's conducting surfaces which voltage can range from less than 100 volts to greater than 10,000 volts. Voltages of 1,000 v, 2,000 v, 3,000 v, 4,000 v, 5,000 v, 6,000 v, 7,000 v, 8,000 v, 9,000 v, 10,000 v, 12,000 v, 15,000 v, 8,000 v can also be used. The voltages can be regulated selectively by hand or an electronic timer from less than one thousands of a second to minutes, hours, and days duration. Electrical timing of the applied voltages can range from a few micro seconds and longer.

The gel film can be made by conventional extrusion, hot melt spin coating, casting, dipping and the like. The artificial muscle made in this manner are useful as contractible muscle elements for small robots which gel film, contracts in thickness and extends in length and width due to the electrostatic forces when a voltage is applied. The gel cylinder increases and decreases in volume thickness so as to expand and contract lengthwise due to the electrostatic forces of the charges on the opposite dielectric surfaces of the gel film. This effect is a function of the dielectric constant of the gel. In order to provide for a muscle with a large strain and therefore a large actuation pressure (greater than 5 MPa). The performance, efficiency and faster response of the cylindrical muscle depends on the amount of strain obtained under elongation. The higher strain under elongation, the better the performance, the better the efficiency, and the faster the response.

Gel muscles actuators made from thin films having greater polyethylene crystallinity are found to produces greater performance, greater efficiency, and faster response than amorphous gels. This result is due to the greater strain performance under elongation. The elongation of the gels of the invention can range from about 100% to greater than 3,000%. The actuation pressure of the actuators made from the gels of the invention can range from about 5 MPa to greater than about 12 MPa. As an example, a 15 layer rolled/folded gel film actuator having a active muscle length of 10 mm and a diameter of 3 mm (made from 0.5 mm thick SEEPS 500 gram Bloom gel) can achieve a stroke of at least about 3 mm and a force of at least about 5 grams.

The strain under elongation of the copolymers forming the gels can range from less than 8 MPa to about 18 MPa and higher as measure at a strain rate of 1000%/min., from less than 5 MPa to about 25 MPa and higher as measure at a strain rate of 100%/min., and from less than 5 MPa to about 30 MPa and higher as measure at a strain rate of 10%.min. Reference (19) reports the fracture strain % and corresponding modulus (Mpa) for Ethylene-styrene copolymers ES16, ES24, ES27, ES28, ES28, and ES30 are 666/52.5, 517/26.4, 453/25, 564/19.5 and 468/25.4 respectively.

The ability to reduce the number of layers, increase strain with elongation, reduce the size of the active muscle actuator and increase the stroke distance at a greater force can be achieved with gels (exhibiting high strain under elongation) made from copolymers having one or more polyethylene components.

The gels of the invention can be formed into gel strands, gel tapes, gel sheets, films, and other articles of manufacture in combination with or without other substrates or materials such as natural or synthetic fibers, multifibers, fabrics, films and the like. Moreover, because of their improved tear resistance and resistance to fatigue, the gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the gels are more tear resistant, they are especially useful for making condoms, toy balloons, and surgical and examination gloves. As toy balloons, the gels are safer because it will not rupture or explode when punctured as would latex balloons which often times cause injures or death to children by choking from pieces of latex rubber. The gels are advantageously useful for making gloves, thin gloves for surgery and examination and thicker gloves for vibration damping which prevents damage to blood capillaries in the fingers and hand caused by handling strong shock and vibrating equipment. The gels are also useful for forming orthotics and prosthetic articles such as for lower extremity prosthesis described below.

The EB copolymer midblock of conventional SEBS is almost totally amorphous and the EP midblock of SEPS is amorphous and non-ethylene.

Gels made from such block copolymers are rubbery and exhibit substantially no hysteresis. Their rubbery-ness and lack of hysteresis are due to the amorphous nature of their midblocks. Such gels are hereafter referred to as "non-ethylene gels" or more simply as "amorphous gels".

In general, the overall physical properties of amorphous gels are better at higher gel rigidities The amorphous gels, however, can fail catastrophically when cut or notched while under applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time.

This physical elastomeric network structure is reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) or (A) and (Y) phases (mesophases) can take the form of spheres, cylinders, lamellae, or bicontinous structures. The scale of separation of the phases are typically of the order of hundreds of angstroms, depending upon molecular weights (i.e. Radii of gyration) of the minority-component segments. The submicron glassy domains which provides the physical interlocking are too small to see with the human eye, too small to see using the highest power optical microscope and only adequately enough to see using the electron microscope. At such small domain scales, when the gel is in the molten state while heated and brought into contact to be formed with any substrate and allowed to cool, the glassy domains of the gel become interlocked with the surface of the substrate. At sufficiently high enough temperatures, with or without the aid of other glassy resins (such as polystyrene homopolymers and the like), the glassy domains of the copolymers forming the gels fusses and interlocks with even a visibly smooth substrate surface such as glass. The disruption of the sub-micron domains due to heating above the softening point forces the glassy domains to open up, unlocking the network structure and flow. Upon cooling below the softing point, the glassy polymers reforms together into sub-micron domains, locking into a network structure once again, resisting flow. It is this unlocking and locking of the network structure on the sub-micron scale with the surfaces of various materials which allows the gel to form interlocking composites with other materials.

A useful analogy is to consider the melting and freezing of a water saturated substrate, for example, foam, cloth, fabric, paper, fibers, plastic, concrete, and the like. When the water is frozen, the ice is to a great extent interlocked with the substrate and upon heating the water is able to flow. Furthermore, the interlocking of the ice with the various substrates on close examination involves interconnecting ice in, around, and about the substrates thereby interlocking the ice with the substrates. A further analogy, but still useful is a plant or weed well established in soil, the fine roots of the plant spreads out and interconnects and forms a physical interlocking of the soil with the plant roots which in many instances is not possible to pull out the plant or weed from the ground without removing the surrounding soil also.

Likewise, because the glassy domains are typically about 200 Angstroms in diameter, the physical interlocking involve domains small enough to fit into and lock with the smallest surface irregularities, as well as, flow into and flow through the smallest size openings of a porous substrate. Once the gel comes into contacts with the surface irregularities or penetrates the substrate and solidifies, it becomes difficult or impossible to separate it from the substrate because of the physical interlocking. When pulling the gel off a substrate, most often the physically interlocked gel remains on the substrate. Even a surface which may appear perfectly smooth to the eye, it is often not the case. Examination by microscopy, especially electron microscopy, will show serious irregularities. Such irregularities can be the source of physical interlocking with the gel.

Such interlocking with many different materials produce gel composites having many uses. The high tear resistant soft gels are advantageously suitable for a safer impact deployable air bag cushions, other uses include: toys; games; novelty, or souvenir items; elastomeric lenses, light conducing articles, optical fiber connectors; athletic and sports equipment and articles; medical equipment and articles including derma use and for the examination of or use in normal or natural body orifices, health care articles; artist materials and models, special effects; articles designed for individual personal care, including occupational therapy, psychiatric, orthopedic, podiatric, prosthetic, orthodontic and dental care; apparel or other items for wear by and on individuals including insulating gels of the cold weather wear such as boots, face mask, gloves, full body wear, and the like have as an essential, direct contact with the skin of the body capable of substantially preventing, controlling or selectively facilitating the production of moisture from selected parts of the skin of the body such as the forehead, neck, foot, underarm, etc; cushions, bedding, pillows, paddings and bandages for comfort or to prevent personal injury to persons or animals; housewares and luggage; articles useful in telecommunication, utility, industrial and food processing, and the like as further described herein.

Health care devices such as face masks for treatment of sleep disorder require non-tacky gels of the invention. The gel 3 forming a gel overlap 7 portion on the face cup 1 at its edge 12 conforming to the face and serve to provide comfort and maintain partial air or oxygen pressure when worn on the face during sleep. Tacky gels because of its tactile feel are undesirable for such applications.

The gels of the invention can be formed into gel strands, gel bands, gel tapes, gel sheets, and other articles of manufacture in combination with or without other substrates or materials such as natural or synthetic fibers, multifibers, fabrics, films and the like. Moreover, because of their improved tear resistance and resistance to fatigue, the gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the gels are more tear resistant, they are especially useful for making condoms, toy balloons, and surgical and examination gloves. As toy balloons, the gels are safer because it will not rupture or explode when punctured as would latex balloons which often times cause injuries or death to children by choking from pieces of latex rubber. The gels are advantageously useful for making gloves, thin gloves for surgery and examination and thicker gloves for vibration damping which prevents damage to blood capillaries in the fingers and hand caused by handling strong shock and vibrating equipment. Various other gel articles can be made from the advantageously tear resistant gels and gel composites of the inventions include gel suction sockets, suspension belts.

The gels are also useful for forming orthotics and prosthetic articles such as for lower extremity prosthesis described below.

Advantageously, the gels of the invention can be made non-tacky requiring no additive. Its non-tackiness are an inherent property of the crystallinity, glassy A components, and selected low viscosity plasticizers forming the gels of the invention. Such gels, however, must met the following criteria:

(a) the gels are made from A-Z-A, (A-Z)n, (A-Y)n, (Y-AY)n and (Y-AY')n copolymers: polyethylene block copolymers and crystalline poly(ethylene-styrene) substantially random copolymers of the type S, M, and E series (for example SEEPS, S-E-EB-S, S-EB$_{45}$-EP-S, S-E-EB$_{25}$-S, S-E-EP-E-S, S-EP-E-S, S-EP-E-EP-S, E-S-E, (E-S)n, (E-S-E)n, (ESP), (ES4M1P), (ESH1), (ESO1), (ESN) and (S-E-EP)n, crystalline S-EB-S with elastomeric crystalline block: glassy block ratios of 89:11, 88:12, 87:13, 86:14, 85:15, 84:16, 83:17, 82:18, 81:19, 80:20, 79:21, 78:22, 77:23, 76:24, 75:25, 74.26, 73:27, 72:28, 71:29, and 70:30) and the like;

(b) the gels are made from copolymers having poly (ethylene) segments exhibit melting endotherm values of at least about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., and higher; and (c) the gels are made from copolymers having glassy A to Y or glassy A to Z ratios of at least 37:63, higher ratios are also of advantage such as 38:62, 39:61, 40:60, 41:59, 42:58, 43:57, 44:65, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34, while lower ratios may also be of advantage (but less so) such as 35:65 and 36:64; or by the addition of (d) sufficient amounts of glassy homopolymers or glass associated phase resins so that condition (c) is met It is believed that the combination of sufficient amounts of crystallinity and sufficient amounts glassy A components of the copolymers in combination with low viscosity plasticizers imparts non-tackiness to the gels of the invention. It is therefore contemplated that the same effect can be achieved by blending highly crystalline and highly glassy copolymers (Dow S, M, & E Series E-S-E), with less crystalline and less glassy copolymers such as amorphous SEPS, SEBS, and amorphous S-EB-EP-S and other amorphous copolymers provided the amorphous copolymers are in minor amounts and there is substantial crystallinity and sufficient over all glassy A components to meet conditions (c).

The glassy homopolymers of (d) are advantageously selected from one or more homopolymers of polystyrene, poly(alpha-methylstyrene), poly(o-methylstyrene), poly(m-methylstryene), poly(p-methylstyrene), and poly (dimethylphenylene oxide) The average molecular weight of the glassy homopolymers advantageously can range from about 2,500 to about 90,000, typical about 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 30,000; 40,000; 50,000; 60,000; 70,000; 80,000; 90,000 and the like. Example of various molecular weights of commercially available polystyrene: Aldrich Nos.:

32,771-9 (2,500M$_w$), 32,772-7 (4,000 Mw), 37,951-4 (13,000 Mw), 32-774-3 (20,000 Mw), 32,775-1 (35,000 Mw), 33,034-5 (50,000 Mw), 32,778-8 (90,000 Mw); poly(alpha-methylstyrene) #41,794-7 (1,300 Mw), 19,184-1 (4,000 Mw); poly(4-methylstyrene) #18,227-3 (72,000 Mw), Endex 155, 160, Kristalex 120, 140 from Hercules Chemical, GE: polyphenylene ether. Blendex 820, HPP825, HPP830, HPP857, HPP820, HPP822, HPP823, and the like. Various glassy phase associating resins having softening points above about 120° C. can also serve to increase the glassy phase of the Gels of the invention and met the non-tackiness critena, these include: Hydrogenated aromatic resins (Regalrez 1126, 1128, 1139, 3102, 5095, and 6108), hydrogenated mixed aromatic resins (Regalite R125), and other aromatic resin (Picco 5130, 5140, 9140, Cumar LX509, Cumar 130, Lx-1035) and the like.

On the other hand, the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Arkon P, Regalrez, Cumar LX, Picco 6000, Nevchem, Piccotex, Kristalex, Piccolastic, LX-1035, and the like.

The commercial resins which can aid in adhesion to materials (plastics, glass, and metals) may be added in minor amounts to the gelatinous elastomer composition, these resins include: polymerized mixed olefins (Super Sta-tac, Betaprene Nevtac, Escorez, Hercotac, Wingtack, Piccotac), polyterpene (Zonarez, Nirez, Piccolyte, Sylvatac), glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035), and the like. More earlier, I had also disclosed the use of liquid tackifiers in high viscosity SEBS gels.

The incorporation of such adhesion resins is to provide strong and dimensional stable adherent gels, gel composites, and gel articles. Typically such adherent gels can be characterized as adhesive gels, soft adhesives or adhesive sealants. Strong and tear resistant adherent gels may be formed with various combinations of substrates or adhere (attach, cling, fasten, hold, stick) to substrates to form adherent gel/substrate articles and composites.

GE polyphenylene ether can be added in minor amounts to the gel to improve crack or craze resistance when the gel is under stress or shear conditions. The amount can vary from less than about 1 part by weight of copolymer to about 15 parts by weight of copolymer. Such amounts include 00.1, 00.2, 00.5, 00.8, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 parts by weight of copolymer(s).

Various substrate and adherent gel combinations (FIGS. 1–4x.) which can be utilized to form composite adherent gel articles include: $G_nM_n$, $G_nG_n$, $G_nM_nG_n$, $M_nG_nM_n$, $M_nG_nG_n$, $G_nG_nM_n$, $G_nG_nM_n$, $G_nM_nM_nG_n$, $M_nG_nG_nM_n$, $M_nM_nG_nG_n$, $M_nM_nM_nG_nG_n$, $G_nM_nG_nG_n$, $G_nM_nG_nM_nM_n$, $M_nG_nM_nG_nM_nG_nM_n$, or any permutations of said combination, where G=gel and M=material. The subscript 1, 2, 3, 4, etc., are different and is represented by n which is a positive number, when n is a subscript of M, n may be the same or different material and when n is a subscript of G, n can be the same or different rigidity adherent gel or the same or different adherent gel material composition. The material (M) suitable for forming composite articles with the gelatinous elastomer compositions can include foam, plastic, fabric, metal, concrete, wood, wire screen, refractory material, glass, synthetic resin, synthetic fibers, and the like. Sandwiches of adherent gel/material (i e adherent gel-material-adherent gel or material-adherent gel-material, etc.) are ideal for use as shock absorbers, acoustical isolators, vibration dampers, vibration isolators, and wrappers. For example the vibration isolators can be use under research microscopes, office equipment, tables, and the like to remove background vibrations.

Various useful adhesion resins of one or more types can be incorporated in minor amounts into the adherent gel. These include: polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, Polyalphamethylstyrene/vinyl toluene copolymer, polystyrene, special resin, and the like.

The adherent gel compositions of the invention can be casted unto various substrates, such as foam, plastic, fabric, metal, concrete, wood, wire screen, refractory material, glass, synthetic resin, synthetic fibers, and the like, or the adherent gels formed and then can be adhere (attach, cling, fasten, hold, stick) to the desired substrates to form various GnMn, GnGn, GnMnGn, MnGnMn, MnGnGn, GnGnMn, GnGnMn, GnMnMnGn, MnGnGnMn, MnMnGnGn, MnMnMnGnGn, GnMnGnGn, GnMnGnMnMn, MnGnMnGnMnGnMn, or any permutations of said combination composites for uses requiring temporary peel and re-use as well as permanent long-life use as needed. Adhesion to substrates is most desirable when it is necessary to apply the adherent gels to substrates in the absence of heat or on to a low temperature melting point substrate for later peel off after use, such as for sound damping of a adherent gel composite applied to a first surface and later removed for use on a second surface. The low melting substrate materials which can not be exposed to the high heat of the molten adherent gels, such as low melting metals, low melting plastics (polyethylene, PVC, PVE, PVA, and the like) can only be formed by applying the adherent gels to the temperature sensitive substrates. Other low melting plastics include. polyolefins such as polyethylene, polyethylene copolymers, ethylene alpha-olefin resin, ultra low density ethylene-octene-1 copolymers, copolymers of ethylene and hexene, polypropylene, and etc. Other cold applied adherent gels to teflon type polymers: TFE, PTFE, PEA, FEP, etc, polysiloxane as substrates are achieved using the adherent gels of the invention.

Likewise, adherent gel substrate composites can be both formed by casting hot onto a substrate and then after cooling adhering the opposite side of the adherent gel to a substrate having a low melting point. The adherent gel is most essential when it is not possible to introduce heat in an heat sensitive or explosive environment or in outer space. The use of solid or liquid resins promotes adherent gel adhesion to various substrates both while the adherent gel is applied hot or at room temperature or below or even under water.

The adherent gels can be applied without heating to paper, foam, plastic, fabric, metal, concrete, wood, wire screen, refractory material, glass, synthetic resin, synthetic fibers, and the like.

The adhesion properties of the gels are determined by measuring comparable rolling ball tack distance "D" in cm using a standard diameter "d" in mm stainless steel ball rolling off an inclined of height "H" in cm and determining the average force required to perform 180° peel of a heat formed $G_1M_1$ one inch width sample applied at room temperature to a substrate $M_2$ to form the composite $M_1G_1M_2$ The peel at a selected standard rate cross-head separation speed of 25 cm/minute at room temperature is initiated at the $G_1M_2$ interface of the $M_1G_1M_2$ composite, where the substrate $M_2$ can be any of the substrates mentioned and $M_1$ preferably a flexible fabric.

Advantageously, glassy phase associating homopolymers such as polystyrene and aromatic resins having low molecular weights of from about 2,500 to about 90,000 can be blended with the triblock copolymers of the invention in large amounts with or without the addition of plasticizer to provide a copolymer-resin alloy of high impact strengths. More advantageously, when blended with multiblock copolymers and substantially random copolymers the impact strengths can be even higher. The impact strength of blends of from about 150 to about 1,500 parts by weight glass phase associating polymer and resins to 100 parts by weight of one or more multiblock copolymers can provide impact strength approaching those of soft metals. At the higher loadings, the impact strength approaches that of polycarbonates of about 12 ft-lb/in notch and higher.

The improvements of the gels of the invention is exceptional, the gels are crystal to the touch and can be quantified using a simple test by taking a freshly cut Gel probe of a selected gel rigidity made from the gels of the invention. The gel probe is a substantially uniform cylindrical shape of length "L" of at least about 3.0 cm formed components (1)–(3) of the gels of the invention in a 16×150 mm test tube. The gel probe so formed has a 16 mm diameter hemi-spherical tip which (not unlike the shape of a human finger tip) is brought into perpendicular contact about substantially the center of the top cover of a new, untouched polystyrene reference surface (for example the top cover surface of a sterile polystyrene petri dish) having a diameter of 100 mm and a weight of 7.6 gram resting on its thin circular edge (which minimizes the vacuum or partial pressure effects of one flat surface in contact with another flat surface) on the flat surface of a scale which scale is tared to zero. The probe's hemi-spherical tip is place in contact with the center of the top of the petri dish cover surface and allowed to remain in contact by the weight of the gel probe while held in the upright position and then lifted up. Observation is made regarding the probe's tackiness with respect to the clean reference polystyrene surface. For purpose of the foregoing reference tack test, tackiness level 0 means the polystyrene dish cover is not lifted from the scale by the probe and the scale shows substantially an equal positive weight and negative weight swings before settling again back to zero with the swing indicated in (negative) grams being less than 1.0 gram. A tackiness level of one 1, means a negative swing of greater than 1.0 gram but less than 2.0 gram, tackiness level 2, means a negative swing of greater than 2 gram but less than 3 gram, tackiness level 3, means a negative swing of greater than 3 gram but less than 4 gram, before settling back to the zero tared position or reading. Likewise, when the negative weight swing of the scale is greater than the weight of the dish (i.e., for the example referred above, greater than 7.6 gram), then the scale should correctly read −7.6 gram which indicates the dish has completely been lifted off the surface of the scale. Such an event would demonstrate the tackiness of a gel probe having sufficient tack on the probe surface. The gels of the invention fails to lift off the polystyrene reference from the surface of the scale when subject to the foregoing reference tack test. Advantageously, the gels of the invention can register a tackiness level of less than 5, more advantageously, less than 3, still more advantageously, less than 2, and still more advantageously less than 1. The non-tackiness of the gels of the invention can advantageously range from less than 6 to less than 0.5 grams, typical tack levels are less than 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5, 2.8, 3.0, 3.5, 4.0, 4.5, 5.0 grams and the like. Whereas probes of gels made from amorphous gels such as SEPS, SEBS, S-EP-EB-S, and the like with copolymer styrene to rubber ratio of less than 37:63 and plasticizer of higher than 30 cSt 40° C. are found to lift the polystyrene reference from the surface of the scale. For purposes of indicating tack, the method above can provide gel tack level readings of 1, 2, 3, 4, 5, 6, and 7 grams. More accurate and sensitive readings can be made using electronic scales of tack levels of less than 1 gram. By this simple method tack levels (of a gel probe on a polystyrene reference surface) can be measure in terms of gram weight displacement of a scale initially tared to zero. For purpose of the present invention the method of using a polystyrene reference surface having a weight of 7.6 grams in contact and being lifted by the tackiness of a cylindrical gel probe having a 16 mm diameter hemi-spherical tip is used to determine the tackiness of the gels of the invention. The level of tack being measured in gram Tack at 23° C.

The improvements of other properties of the gels over amorphous gels are many, these include: improved damage tolerance, improved crack propagation resistance, improved tear resistance, improved resistance to fatigue, etc Such gels are advantageous for end-use involving repeated applications of stress and strain resulting from large number of cycles of deformations, including compression, compression-extension (elongation), torsion, torsion-compression, torsion-elongation, tension, tension-compression, tension-torsion, etc. The gels also exhibit improved damage tolerance, crack propagation resistance and especially improved resistance to high stress rupture which combination of properties makes the gels advantageously and surprisingly exceptionally more suitable than amorphous gels made from non-poly(ethylene) component copolymers at corresponding gel rigidities.

Block copolymers with polyethylene midblocks alone do not form suitable Gels for purpose of the invention. Polyethylene midblock regions needs to be balanced with amorphous midblock regions in order to obtain soft, flexible and elastic gels with the desired tear resistant properties that are not found in totally amorphous gels.

The various representative polyethylene/glassy domain/amorphous structures of S-E-EB-S, S-E-EB$_{25}$-S, S-E-EP-E-S, S-EP-E-S and S-EP-E-EP-S. Although the structure are spheroid representation, cylinders and plates are also within the scope of the present invention. Cylinder and plate structure are obtained with increasing glassy A end blocks. From about 15–30% by weight of A blocks, the block copolymer structure is spheroid. From about 33 about 40% by weight of A blocks, the block copolymer structure becomes cylindrical; and above about 45% A blocks, the structure becomes less cylindrical and more plate like.

Generally, one or more (E) midblocks can be incorporated at various positions along the midblocks of the block copolymers. Using the sequential process for block copolymer synthesis, The (E) midblocks can be positioned as follows:

| | |
|---|---|
| a) | A-E-W-A |
| b) | A-E-W-E-A |
| c) | A-W-E-W-A |
| d) | A-E-W-E-W-E-W-E-A |
| e) | A-W-E-W-A-E-A-E-W-E-A |
| f) | and etc. |

The lower flexibility of block copolymer gels due to (E) midblocks can be balanced by the addition of sequentially (W) midblocks. For example, the sequentially synthesized block copolymer SE-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, (S-EP)n and the like can produce more softer, less rigid, and more flexible gel.

Because of the (E) midblocks, the gels of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the gels when stretched exhibit additional yielding as shown by necking caused by stress induced crystallinity. Additionally, the crystallization rates of the crystalline midblocks can be controlled and slowed depending on thermal history producing time delay recovery upon deformation.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and gels to deformation cycles to failure (appearance of cracks, crazes, rips or tears in the gels).

The invention gels can be made to exhibit sufficient low Gram Tack to be noticeable non-tacky to the touch of the fingers of a typical human hand at 23° C. A simple way to accurately measure the non tacky feeling as sensed by the fingers is to drop a reference gel sample having a cylindrical shape of about 1.0 cm diameter and 1.0 cm in length a distance of 10 cm on to the surface of a polystyrene petri dish having a diameter of 10 cm inclined at 45°. The reference gel sample is considered non tacky if it (1) "bounce at least twice before coming to rest", (2) "bounce off", (3) "bounce and then rolls off", or (4) "rolls off" on striking the polystyrene surface. If none of (1) thru (4) is observed, then the level of Gram Tack can be determined by the gel sample method above.

The invention gel composition comprises at least one high viscosity linear multiblock copolymers and star-shaped (or radial) multiblock copolymers The invention gel compositions copolymer (I) comprises 100 parts by weight of one or a mixture of two or more of a hydrogenated styrene isoprene/butadiene block copolymer(s) more specifically, hydrogenated styrene block polymer with 2-methyl-1,3-butadiene and 1,3-butadiene) or poly(styrene-ethylene-ethylene-propylene-styrene) SEEPS or poly(styrene-ethylene-ethylene-propylene)$_n$, (SEEP)$_n$.

In general such block copolymers have the general configurations $A^n$-Z-$A^n$ and $(A^n$-Z)$_n$ wherein each $A^n$ is a selected glassy polymer end block of a monoalkenyl arene compounds, more specifically, a monovinyl aromatic compounds such as polystyrene (where superscript n=1), monovinylnaphithalene as well as the alkylated derivatives thereof such as poly(alpha-methylstyrene) (n=2), poly(o-methylstyrene) (n=3), poly(m-methylstryene) (n=4), poly(p-methylstyrene) (n=5) poly(tertiary-butylstyrene) (n=6), and the like, and midblocks (Z) comprising polymer chains of poly(ethylene), poly(ethylene) and poly(propylene) or -EEP-. In the case of styrene glassy end blocks, the hydrogenated styrene isoprene/butadiene block copolymer(s) have the formula The SEEPS (I) linear copolymers are characterized as having a Brookfield Viscosity value at 5 weight percent solids solution in toluene at 30° C. of from less than about 40 cps to about 150 cps and higher, advantageously from about 40 cps to about 60 cps and higher, more advantageously from about 50 cps to about 80 cps and higher, still more advantageously from about 70 cps to about 110 cps and higher, and even more advantageously from about 90 cps to about 180 cps and higher.

The (I) star-shaped copolymers are characterized as having a Brookfield Viscosity value at 5 weight percent solids solution in toluene at 30° C. of from about 150 cps to about 380 cps and higher, advantageously from about 150 cps to about 260 cps and higher, more advantageously from about 200 cps to about 580 cps and higher, and still more advantageously from about 500 cps to about 1,000 cps and higher.

This physical elastomeric network structure of the invention gels are reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) phases (mesophases) can take the form of spheres, cylinders, lamellac, or bicontinous structures. The scale of separation of the phases are typically of the order of hundreds of angstroms, depending upon molecular weights (i.e Radii of gyration) of the minority-component segments. The sub-micron glassy domains which provides the physical interlocking are too small to see with the human eye, too small to see using the highest power optical microscope and only adequately enough to see using the electron microscope. At such small domain scales, when the gel is in the molten state while heated and brought into contact to be formed with any substrate and allowed to cool, the glassy domains of the gel become interlocked with the surface of the substrate. At sufficiently high enough temperatures, with or without the aid of other glassy resins (such as polystyrene homopolymers and, the like), the glassy domains of the copolymers forming the invention gels fusses and interlocks with even a visibly smooth substrate surface such as glass. The disruption of the sub-micron domains due to heating above the softening point forces the glassy domains to open up, unlocking the network structure and flow. Upon cooling below the softening point the glassy polymers reforms together into sub-micron domains, locking into a network structure once again, resisting flow. It is this unlocking and locking of the network structure on the sub-micron scale with the surfaces of various materials which allows the gel to form interlocking composites with other materials.

A useful analogy is to consider the melting and freezing of a water saturated substrate, for example, foam, cloth, fabric, paper, fibers, plastic, concrete, and the like. When the water is frozen, the ice is to a great extent interlocked with the substrate and upon heating the water is able to flow. Furthermore, the interlocking of the ice with the various substrates on close examination involves interconnecting ice in, around, and about the substrates thereby interlocking the ice with the substrates. A further analogy, but still useful is a plant or weed well established in soil, the fine roots of the plant spreads out and interconnects and forms a physical interlocking of the soil with the plant roots which in many instances is not possible to pull out the plant or weed from the ground without removing the surrounding soil also.

Likewise, because the glassy domains are typically about 200 Angstroms in diameter, the physical interlocking involve domains small enough to fit into and lock with the smallest surface irregularities, as well as, flow into and flow through the smallest size openings of a porous substrate. Once the gel comes into contacts with the surface irregularities or penetrates the substrate and solidifies, it becomes difficult or impossible to separate it from the substrate because of the physical interlocking. When pulling the gel off a substrate, most often the physically interlocked gel remains on the substrate. Even a surface which may appear perfectly smooth to the eye, it is often not the case Examination by microscopy, especially electron microscopy, will show serious irregularities. Such irregularities can be the source of physical interlocking with the gel.

The polyethylene midblock containing block copolymers of the invention gel are the result of hydrogenation of butadiene. In order for the block copolymers forming the invention gel to exhibit polyethylene crystallinity, the midblock segments must contain long runs of —$CH_2$— groups. There should be approximately at least 16 units of —($CH_2$)— in sequence for crystallinity. Only the (—$CH_2$—)$^4$ units can crystallize, and then only if there are at least 4 units of (—$CH_2$—)$^4$ in sequence; alternatively, the polyethylene units are denoted by [—($CH_2$—$CH_2$—$CH_2$—$CH_2$)—]$^4$, [(—$CH_2$—)$^4$]$^4$ or (—$CH_2$—)$^{16}$.

The polyethylene crystalline segments or midblocks of copolymers forming the invention gel can be characterized by the presence of a melting trace of from less than about 2.5° C. (for low viscosity polyethylene midblock containing block copolymers) to greater than about 18° C. (for higher viscosity polyethylene midblock containing block copolymers) as determined by crystallization exotherm DSC curve. More specific DSC melting values of the crystalline midblock block segment of the SEEPS copolymers may be carefully measured and detected include less than about 1.5° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., and higher. Whereas, the melting trace in DSC evidencing the presence of crystalline polyethylene are not found in amorphous block copolymers such as SEPS.

The crystallization exotherm of the crystalline block copolymer invention gel are determined by ASTM D 3417 method. In order to provide conditions for DSC samples of certain polyethylene midblock containing block copolymers to have the best possible chance to exhibit any crystallinity the measurement protocol can be modified as follows: heat to 140° C. @10° C./min., cool to 0° C. @2° C./min, put sample in freezer for 1 week, heat sample to 140° C. @1° C./min, then cool to 0° C./min.

Generally, the method of obtaining long runs of crystalline —($CH_2$)— is by sequential block copolymer synthesis followed by hydrogenation. The attainment of invention gels is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalline midblocks of the final block copolymers.

The crystalline block copolymers are made by sequential block copolymer synthesis, the percentage of crystallinity or (—$CH_2$—)$^{16}$ units should be at least about $(0.67)^4$ or about 20% and actual crystallinity of about 12%. For example, a selective synthesized S-EBn-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of (—$CH_2$—)$^4$ units, eg, n=33 or 20% crystallinity which is the percentage of $(0.67)^4$ or "(—$CH_2$—)$^{16}$" units. Thus, when n=28 or 72% of (—$CH_2$—)$^4$ units, the % crystallinity is $(0.72)^4$ or 26.87% crystallinity attributed to (—$CH_2$—)$^{16}$ units, denoted by -EB$_{28}$-. As a matter of convention, and for purposes of this specification involving hydrogenated polybutadiene: the notation -E- denotes at least about 85% of (—$CH_2$—)$^4$ units. The notation -B- denotes at least about 70% of [—$CH_2$—$CH(C_2H_5)$—] units. The notation -EB- denotes between about 15 and 70% [—$CH_2$—$CH(C_2H_5)$—] units. The notation -EBn- denotes n% [—$CH_2$—$CH(C_2H_5)$—] units, For hydrogenated polyisoprene. The notation -EP- denotes about at least 90% [—$CH_2$—$CH(CH_3)$—$CH_2$—$CH_2$—] units.

Generally, one or more (E) midblocks can be incorporated at various positions along the midblocks of the block copolymers. The lower flexibility of block copolymer gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock may be crystalline and flexibility low, physical blending with amorphous block copolymers such as S-EP-S, S-EB-EP-S, (S-EP)$_n$ and the like can produce more softer, less rigid, and more flexible gel.

Because of the high viscosity of the block copolymers and (E) midblocks, the invention gel exhibit different physical characteristics and improvements over amorphous gels including damage tolerance, improved crack propagation resistance, improved tear resistance producing knotty tears as opposed to smooth tears, improved resistance to fatigue, higher hysteresis, etc. Moreover, the invention gels when stretched exhibit additional yielding as shown by necking caused by stress induced crystallinity or yielding of the styrene glassy phases.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis.

Block Copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of —$CH_2$— groups and negligible crystallinity, ie, about $(0.5)^4$ or 0.06 or 6% and actual crystallinity of about 3%. Due to the constraints of Tg and minimum hysteresis, conventional S-EB-S have ethylene-butylene ratios of about 60:40 with a crystallinity of about $(0.6)^4$ or 0.129 or 12% and actual crystallinity of about 7.7%.

Block Copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —$CH_2$— and no crystallinity.

Mixed Block Copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

Block Copolymer S-EEP-S

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)^4$ or 5.3%. The actual crystallinity would be approximately about 3.2%, which is negligible and results in a good rubbery midblock. This theoretical % of actual crystallinity corresponds well to commercially available SEEPS Septon 4033 and 4055 which varies with batch lots.

For purpose of convince and simplicity, the hydrogenated polybutadiene are denoted as follows: -E- denotes at least 85% R-1 units, -B- denotes at least 70% R-2 units, -EB- denotes between 15 and 70% R-2 units, -EBn- denotes n% R-2 units, and -EP- denotes 90% R-3 units.

Table I below gives the % of units on hydrogenation of polybutadiene/polyisoprene copolymer midblocks $$|H2$$

$$—(CH_2)4—(CH—CH_2)——(CH_2—CH—CH_2—CH_2)—(CH_2—CH)—$$

$$C_2H_5 \qquad\qquad CH_3 \quad CH$$
$$\qquad\qquad\qquad\qquad CH_3CH_3$$

n % from polybutadiene (1−n)% from polyisoprene
90%·n 10%·n 95%·(1−n) 5%·(1−n)

where n is the mole % polybutadiene in the polybutadiene-polyisoprene starting polymer

| n = | R-1 | R-2 | R-3 | R-4 |
|---|---|---|---|---|
| 0% | 0% | 0% | 95% | 5% |
| 20% | 18% | 2% | 76% | 4% |
| 40% | 36% | 4% | 57% | 3% |
| 60% | 54% | 6% | 38% | 2% |
| 80% | 72% | 8% | 19% | 1% |
| 100% | 90% | 10% | 0% | 0% | where R-1 denotes $(—CH_2—)^4$,
R-2 denotes —(CH—$CH_2$)—, $$C_2H_5$$

R-3 denotes —($CH_2$—CH—$CH_2$—$CH_2$)—, and $$CH_3$$

R-4 denotes —($CH_2$—CH)—

$$CH$$

$$CH_3CH_3$$

Therefore, the percentage that can crystallize is $[(—CH_2—)^4]^4$ since this is the chance of getting four $(—CH_2—)^4$ units in sequence. The percentage that will crystallize is about 60% of this.

| n = | $(—CH_2—)^4$ | $[(—CH_2—)^4]^4$ | $0.6 \times [(—CH_2—)^4]_n$ |
|---|---|---|---|
| 0% | 0% | 0% | 0% |
| 20% | 18% | 0.1% | 0.06% |
| 40% | 36% | 1.7% | 1.0% |
| 60% | 54% | 8.5% | 5.1% |
| 80% | 72% | 26.9% | 16.1% |
| 100% | 90% | 65.6% | 39.4% |

This applies to polymerization in a hydrocarbon solvent. In an ether (eg, diethylether), the percentage $(-CH_2-)^4$ units will be reduced so that crystallinity will be negligible.

| n = | $(-CH_2-)^4$ | $[(-CH_2-)^4]^4$ | $0.6 \times [(-CH_2-)^4]^4$ |
|---|---|---|---|
| 0% | 0% | 0% | 0% |
| 20% | 5% | 0.0006% | 0.0004% |
| 40% | 10% | 0.01% | 0.006% |
| 60% | 15% | 0.05% | 0.03% |
| 80% | 20% | 0.16% | 0.10% |
| 100% | 25% | 0.39% | 0.23% |

These values are all negligible. There will be no detectable crystallinity in any of these polymer midblocks. In a mixed ether/hydrocarbon solvent, values will be intermediate, depending on the ratio of ether to hydrocarbon.

The midblock components (Z) can comprise various combinations of midblocks between the selected end blocks (A); these include: -E-EB-, -E-EP-, -E-EP-E-, -E-EB-E-, -E-E-EP-, -E-E-EB-, and the like.

The (Z) midblock of two or more polymer chains can be obtained by hydrogenation methods, for example: 1,4-polybutadiene ($B_{1,4}$) can be converted by hydrogenation to poly(ethylene), 1,4-polybutadiene ($B_{1,4}$) and 1,2-polybutadiene ($B_{1,2}$) can be converted by hydrogenation to poly(ethylene-butylene), 1,4-poly-isoprene ($I_{1,4}$) can be converted by hydrogenation to poly(ethylene-propylene), 1,2-polybutadiene ($B_{1,2}$) can be converted by hydrogenation to atactic poly(1-butene)(polybutylene), 1,4-polybutadiene ($B_{1,4}$) and polyisoprene (I) 1,4-poly-butadiene ($B_{1,4}$) can be converted by hydrogenation to poly(ethylene-ethylene-co-propylene-ethylene), 2-methyl-1,3-polybutadiene and 1,3-polybutadiene (I, $B_{1,3}$) can be converted by hydrogenation to poly(ethylene-ethylene-co-propylene), and the like. Polypropylene can be modified by tailblocking a poly(ethylene-propylene) copolymer segment on the propylene block to form poly(propylene-ethylene-co-propylene); likewise, poly(ethylene-propylene)$_n$ (EP), poly(propylene-ethylene-co-propylene-propylene) (P-EP-P), poly(propylene-ethylene-propylene) (P-E-P), poly(ethylene-ethylene-copropylene) (E-EP) can be formed. It is noted herein that B (bold) denotes polybutadiene and B (plain) denotes polybutylene.

Further, the multiblock copolymers ($A^n$-Z-$A^n$) can be obtained by various synthesis methods including hydrogenation of selected block copolymers. When the subscript n of A is=1, (polystyrene) (S), for example, suitable block copolymers can be converted to the useful multiblock copolymers forming the invention gels. These include: conversions of S-I-$B_{1,3}$-S to (S-E-EP-S), S-$B_{1,4}$-I-$B_{1,4}$-S to (S-E-EP-E-S), S-$B_{1,2}$-I-S to (S-B-EP-S), S-$B_{1,3}$-$B_{1,2}$-$B_{1,4}$-S to (S-E-EB-S), S-$B_{1,4}$-$B_{1,2}$-I-S to (S-EB-EP-S), S-I-$B_{1,3}$-$B_{1,2}$-$B_{1,4}$-S to (S-E-EP-EB-S), etc. As denoted herein abbreviations are interchangeably used, for example, (S-E-EP-S) denotes poly(styrene-ethylene-ethylene-co-propylene-styrene). Other linear multiblock copolymers (denoted in abbreviations) can be formed, including: (S-B-EB-S), (S-E-EB-E-S), (S-B-EP-E-S), (S-B-EB-E-S), (S-E-E-EP-S), (S-E-E-EB-S), and the like.

The multiblock star-shaped (or radial) copolymers ($A^n$-Z)$_n$ can be obtained by various synthesis methods including hydrogenation of selected block copolymers. When the subscript n of A is=1, (polystyrene) (S), for example, suitable block copolymers can be converted to the useful multiblock copolymers forming the invention gels. These include: conversions of (S-I-$B_{1,3}$)$_n$ to poly(styrene-ethylene-ethylene-co-propylene)$_n$ denoted by the abbreviation (S-E-EP)$_n$, (S-$B_{1,4}$-I-$B_{1,4}$)$_n$ to (S-E-EP-E)$_n$, S-$B_{1,2}$-I)$_n$ to (S-B-EP)$_n$, (S-$B_{1,3}$-$B_{1,2}$-$B_{1,4}$)$_n$ to (S-E-EB)$_n$, (S-$B_{1,4}$-$B_{1,2}$-I)$_n$ to (S-EB-EP)$_n$, (S-I-$B_{1,3}$-$B_{1,2}B_{1,4}$)$_n$ to (S-E-EP-EB)$_n$, etc. Other multiblock copolymers can be formed, including: (S-B-EB)$_n$, (S-E-EB-E)$_n$, (S-B-EP-E)$_n$, (S-B-EB-E)$_n$, (S-B-EP-B)$_n$, (S-B-EB-B)$_n$, (S-E-E-EP)$_n$, (S-E-E-EB)$_n$, (S-B-E-EP)$_n$, (S-B-E-EB)$_n$, (S-B-B-EP)$_n$, (S-B-B-EB)$_n$, (S-E-B-EB)$_n$, (S-E-B-EP)$_n$, (S-EB-EB)$_n$, (S-EP-EP)$_n$, (S-E-EB-EB)$_n$, (S-E-EP-EP)$_n$, (S-E-EB-EP)$_n$, (S-B-EB-EB)$_n$, (S-B-EP-EP)$_n$, and the like.

The Z and A portions of the linear and star-shaped multiblock copolymers are incompatible and form a two or more-phase system consisting of sub-micron glassy domains (A) interconnected by flexible Z chains. These domains serve to crosslink and reinforce the structure. This physical elastomeric network structure is reversible, and heating the polymer above the softening point of the glassy domains temporarily disrupt the structure, which can be restored by lowering the temperature.

It should be noted that when the A to Z ratios falls substantially below about 30:70, various properties such as elongation, tensile strength, tear resistance and the like can decrease while retaining other desired properties, such as gel rigidity, flexibility, elastic memory.

In general, for these block copolymers, the various measured viscosities of 5, 10, 15, and 20, weight percent solution values in toluene at 30° C. can be extrapolated to a selected concentration. For example, a solution viscosity of a 5 weight percent copolymer solution in toluene can be determined by extrapolation of 10, 15, and 20 weight percent measurements to 5 weight percent concentration.

The Brookfield Viscosities can be measured at various neat polymer concentrations, for example, the selected high viscosity linear multiblock copolymers in (I) can have a typical Brookfield Viscosity value of a 20 weight percent solids solution in toluene at 25° C. of about 1,800 cps and higher, and advantageously about 2,000 cps and higher. Typically, the Brookfield Viscosity values can range from at least about 1,800 to about 16,000 cps and higher. More typically, the Brookfield Viscosity values can range from at least about 1,800 cps to about 40,000 cps and higher. Still more typically, the Brookfield Viscosity values can range from at least about 1,800 cps to about 80,000 cps and higher. Due to structural variations between the multiblock and star-shaped copolymers, the high viscosity star-shaped or radial copolymers, typically, may exhibit a lower Brookfield Viscosity value than its counterpart linear multiblock copolymers. However, when the multiblock copolymers are considered as star-shaped or branched, than at equal branch lengths, the solution viscosities of the multiblock copolymers and branched copolymers are about the same or equivalent.

In all cases, the molecular chain lengths (molecular weights) of the multiblock and star-shaped (or radial) copolymers (I) must be sufficient to meet the high solution Brookfield Viscosities requirements described herein that is necessary for making the soft, strong and extreme tear resistant gels.

The copolymers (I) selected have Brookfield Viscosity values ranging from about 1,800 cps to about 80,000 cps and higher when measured at 20 weight percent solution in toluene at 25° C., about 4,000 cps to about 40,000 cps and higher when measured at 25 weight percent solids solution in toluene. Typical examples of Brookfield Viscosity values for star-shaped copolymers at 25 weight percent solids solution in toluene at 25° C. can range from about 3,500 cps to about 30,000 cps and higher; more typically, about 9,000 cps and higher. Other advantageous multiblock and multiblock star-shaped copolymers can exhibit viscosities (as measured with a Brookfield model RVT viscometer at 25° C.) at 10 weight percent solution in toluene of about 400 cps and higher and at 15 weight percent solution in toluene of about 5,600 cps and higher. Other advantageous multiblock and star-shaped copolymers can exhibit about 8,000 to about 20,000 cps at 20 weight percent solids solution in toluene at 25° C. Examples of most advantageous high viscosity linear multiblock copolymers can have Brookfield viscosities at 5 weight percent solution in toluene at 30° C. of from about 40 to about 50, 60, 70, 80, 90, 100. 120, 150, 200 cps and higher, while viscosities of star-shaped multiblock copolymers are 150 cps and higher.

Examples of high viscosity multiblock copolymers (I) having two or more midblocks are Kuraray's (S-E-EP-S) 4033, 4045, 4055 and 4077 hydrogenated styrene isoprene/butadiene block copolymers, more specifically, hydrogenated styrene block polymer with 2-methyl-1,3-butadiene and 1,3-butadiene. Kuraray's 4055 (S-E-EP-S) multiblock copolymer and 4077 exhibit viscosities at 5 weight percent solution in toluene at 30° C. of about 90 cps to about 120 cps and about 200 to about 380 cps respectively. At 10 weight percent SEEPS 4055 is about 5,800 cps and higher. Other linear and star multiblock copolymers (I) such as (S-E-EP-S), (S-E-EP-E-S), (S-B-EP-S), (S-E-EB-S), (S-EB-EP-S), (S-E-EP-EB-S), (S-B-EB-S), (S-E-EB-E-S), (S-B-EP-E-S), (S-B-EB-E-S), (S-B-EP-B-S), (S-B-EB-B-S), (S-E-E-EP-S), (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EB-EP-S), (S-B-EP-EB-S), (S-E-EP-E-EP-S), (S-E-EP)$_n$, (S-E-EP-E)$_n$, (S-B-EP)$_n$, (S-E-EB-S)$_n$, (S-EB-EP-)$_n$, (S-E-EP-EB)$_n$, (S-B-EB)$_n$, (S-E-EB-E)$_n$ can also exhibit viscosities at 5 weight percent solution in toluene at 30° C. of from less than about 100 to about 200, 300, 400, 500, 600, 700, 800, 900, 1,000, 1,200, 1,300, 1,600, 1,800, 2,000 cps and higher.

The copolymer (I) forming the invention gels can have a broad range of A end block to Z center block ratio of about 20.80 or less to about 40:60 or higher. The A:Z weight ratios can range from lower than about 20:80 to above about 40:60 and higher. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Broadly, the styrene block to elastomeric block ratio A:Z of the high viscosity multiblock and star copolymers (I) is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 30:70.

Theory notwithstanding, the multiblock copolymer gel properties can be attributed to the additional blocks affecting the separate polymer phases, the additional blocks affecting the heterophase structure, the additional blocks affecting the interfacial regions between phases of the multiblock polymers, the additional blocks forming a separate phase or inducing the formation of additional separate phases, or the high molecular weight and combination of high styrene content of the block copolymer. Due to the additional number of midblocks of the copolymers (I), the differences in solubility parameters between (A) and (Z) becomes greater than the solubility parameters differences between (A) and (D) of triblock copolymers, where D denotes the lone midblock polymer chain. Moreover, the presence of additional midblocks of ethylene, propylene, butylene, ethylene-propylene, or ethylene-butylene may contribute to stress-induced crystallization. This may explain why as the viscosity of the multiblock copolymers is increased to a higher level, the appearance of the invention gels change from clear to more translucent white.

The invention gels of the present invention resist tearing under tensile loads or dynamic deformation in that when cut or notched, the "crack" made on the gel deep surface does not readily propagate further under dynamic deformation or tensile loads. Unlike triblock copolymer gels, such as (SEBS) and (SEPS) gels which possess high tensile strength and will catastrophically snap apart into two reflective clean smooth surfaces when cut or notched under tensile or dynamic loads. Furthermore, when elongated, the invention gels can exhibit two or more draw plateaus and can possess high tensile strength and rapid return from high extension without noticeable set or deformation. As observed, the invention gels can be stretched by a first tensile load with uniform deformation to a measured length, upon the application of higher tensile loads, the gel can be further extended without breaking. Upon release, the gel returns immediate to its original shape and any necking quickly disappears. Again, theory notwithstanding, the additional drawing plateaus of the gel may be attributed to yielding of crystallite formations ethylene or propylene components in the gel or yield of induced interfacial regions of concentrated ethylene or propylene between the domains which during extension absorbs the elastic energy. Likewise, the resistance to tear propagation of the invention gels when notched under tensile load can be attributed to yielding of the gel midblock components, yielding of additional phases, or yielding of interfacial regions before rupture or deformation of the (A) domains can take place.

Additionally, shearing, heating or cooling form the molten state can alter the gels' state. The invention gels can be made to exhibit long elastomeric recovery times. Such gels can be used effectively in suppressing low frequency vibrations and for absorbing energy. The unusual properties of the invention gels can be attributed to altering different phase or interfacial arrangements of the domains of the multiblock copolymers. The presence of polyethylene and crystallinity in block copolymers can be determined by NMR and DSC.

Physical measurements (NMR and DSC) of typical commercial Kraton G 1651, Septon 2006, Septon 4033 and Septon 4055 block were performed. Two types of $^{13}$C NMR spectra data were collected. The gated decoupled experiment provided quantitative data for each type of carbon atom. The DEPT experiment identified each type of carbon atom having attached protons. The DEPT data allowed assignment of the resonances in the gated decoupled experiment, which was then integrated for quantitation of the different types of midblock and end groups in each polymer tested The relative quantities of each type of carbon group in the various polymers were found. The uncertainty associated with these measurements is estimated as ±3 percentage units. Only the Kraton 1651 spectrum had resonances below about 20 ppm. These resonances, at 10.7–10.9 ppm, were assigned to the butylene methyl group and distinguish the SEBS polymer from the SEPS and SEEPS types of polymer (36). Only the Septon 2006 spectrum lacked the resonance at about 20 ppm that is characteristic of polyethylene units (defined here as three contiguous CH$_2$ groups), and this feature distinguishes the SEPS polymer from the SEBS and SEEPS polymers (36). There were additional differences between the spectra. The Septon 2006 and the Septon 4033 and 4055 spectra all showed resonances at 20 ppm; whereas the spectrum of Kraton 1651 was missing this resonance The 20 ppm peak is characteristic of the methyl group of a propylene subunit, which is present in SEPS and SEEPS polymers but absent in the SEBS polymer. There were also a methylene peak, at 24.6 ppm, and a methine peak at 32.8 ppm, in all of the Septon spectra but not in the Kraton 1651 spectra. These resonances also arise from the propylene subunit.

The chemical shifts, relative intensities, and relative integrations were the same for the spectra of the Septon 4033 and Septon 4055, indicating that these two polymeric compositions are identical based on NMR spectroscopy.

DSC of ASTM D3417-99 was modified to provide conditions for the samples to have the best possible chance to exhibit any crystallinity. The protocol was as follows: (1) heat to 140° C. @10° C./min., (2) cool to 0° C. @2° C./min., (3) place in freezer for 1 week, (4) heat to 140° C. @1° C./min, and (5) cool to 0° C. @1° C./min.

This protocol was used with the exception that the samples were left in the freezer for approximately 2 months, instead of 1 week, because the DSC equipment broke during the week after the first run and required some time for repair. This delay is not expected to have negatively impacted the results of the experiment.

Two HDPE reference samples gave clearly defined crystallization exotherms and fusion endotherms, allowing calculation of heats of crystallization and fusion. These results showed that the equipment and methodology were fully functional, and this check was performed daily during DSC operation. Of the samples, only Kraton 1651 showed discernable transitions for both crystallization and fusion. The Septon 2006 showed no discernable transitions, which is consistent with its SEPS structure being entirely amorphous. The Septons 4033 and 4055 showed crystallization exotherms.

The heats of crystallization for the Kraton 1651 and Septons 4033 and 4055 were small, below about 3 J/g, indicating that small amounts of crystallinity are present in these polymers. The DSC data show:

Kraton 1651: crystallization exotherm peak at 18.09° C., crystallization exotherm—mass normalized enthalpy (J/g) of 1.43, fusion endortherm peak at 34.13° C., and Fusion Endotherm—mass normalized enthalphy J/g of 15.17.

Septon 2006: crystallization exotherm peak (not detected), crystallization exotherm—mass normalized enthalpy (not detected), fusion endortherm peak NONE, and Fusion Endotherm—mass normalized enthalphy (not detected).

Septon 4033: crystallization exotherm peak at 2.86° C., crystallization exotherm—mass normalized enthalpy (J/g) of 3.00, fusion endortherm peak (not detected), and Fusion Endotherm—mass normalized enthalphy (not detected).

Septon 4055: crystallization exotherm peak at 14.4° C., crystallization exotherm—mass normalized enthalpy (J/g) of 1.32, fusion endortherm peak (not detected), and Fusion Endotherm—mass normalized enthalphy (not detected).

Aldrich 13813JU polyethylene reference: crystallization exotherm peak at 119.72° C., crystallization exotherm—mass normalized enthalpy (J/g) of 174.60, fusion endortherm peak at 130.70° C., and Fusion Endotherm—mass normalized enthalphy J/g of 189.90.

Plasticizers (II) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Incorporated herein by reference, in part, is the "Physical and Chemical Properties of Mineral Oils That Affect Lubrication", © Copyright Herguth Laboratories, Inc. 1995, which is a review of mineral oils and terms for the tribologist working in the field of Tribology. A few of the terms are provided for clear reading of the description of the invention as follows:

Viscosity is the property of a fluid that causes it to resist flow, which mechanically is the ratio of shear stress to shear rate. Viscosity may be visualized as a result of physical interaction of molecules when subjected to flow. Lubricating oils have long chain hydrocarbon structures, and viscosity increases with chain length. The unit of absolute or dynamic viscosity is Force/Area×Time. The basic SI unit is Pascal× second Pa s (or Ns m−2). Mineral oils are typically 0.02 to 0.05 Pa.s at 40 degree C. 1 mPa.s=1 Centipoise (cP) cP is commonly used for absolute viscosity. The symbol for viscosity is usually u. When gravity is used to cause flow for the viscosity measurement, the density p of the oil is involved and kinematic viscosity is reported=u/p. The basic SI unit is meter$^2$/second (m2 s−1). Also 1 cm2 s−1=1 Stoke (St), and 1 mm2 s−1=1 centiStoke (cSt), cSt is commonly used for kinematic viscosity. Viscosity (by ASTM D445) of industrial lubricants is commonly classified using the International Standard Organization Viscosity Grade (ISOVG) system, which is the average viscosity in centiStokes (cSt) at 40 degree C. For example, ISOVG 32 is assigned to oils with viscosity between 28.8 and 35.2 cSt at 40 degree C.

Viscosity Index (VI) is a commonly used expression of an oil's change of viscosity with temperature. VI is based on two hypothetical oils with arbitrarily assigned VI's of 0 and 100. The higher the viscosity index the smaller the relative change in viscosity with temperature. A less arbitrary indication of the change in viscosity with temperature is the viscosity temperature coefficient. For 40 to 100 degree C. it is: Viscosity (cSt) at 40 degree C. minus Viscosity (cSt) at 100 degrees C.=C−1, divided by the Viscosity (cSt) at 40 degrees C.

Vapor pressure is the pressure exerted by a vapor on a liquid when it is in equilibrium with its own vapor. The higher the concentration of low molecular weight fractions, the greater the vapor pressure. Vapor pressure is reported as a pressure at a specified temperature. Volatility is reported as percent evaporative weight loss and is measured by ASTM method D-972.

Flash point is an indication of the combustibility of the vapors of a mineral oil, and is defined as the lowest temperature at which the vapor of an oil can be ignited under specified conditions. Flash point is clearly related to safety. Flash point of lubricating oils is measured using ASTM D 92. An open cup of oil is heated at a specific rate while periodically passing a small flame over its surface. The flash point is considered to be the lowest temperature at which the oil vapors will ignite, but not sustain a flame.

Surface tension is the surface energy between a liquid and its own vapor, or air, or a metal surface. The word tension comes from the force that resists any attempt to increase the surface area. Surface tension is thought to be a factor in the ability of an oil to "wet" a surface, in emulsion stability, and in the stability of dispersed solids. However, "wetting" has been found to be a complex phenomenon involving oleophobic and oleophilic films on the metal surface. Some additives markedly change surface tension.

Paraffinic oils are straight chain or branched aliphatic hydrocarbons belonging to the series with the general formula CnH2n+2. Paraffin's are saturated with respect to hydrogen. A typical paraffinic oil molecule with 25 carbon and 52 hydrogen atoms has a molecular weight of 352. Very high molecular weight paraffins are solid waxes, also dissolved in small amounts of mineral oils.

Naphthenic or alicyclic oils have the characteristics of naphthenes, which are saturated hydrocarbons of which the molecules contain at least one closed ring of carbon atoms.

Paraffins are relatively unreactive and thus have better oxidation stability compared to naphthenes. In general, paraffins have a higher viscosity index than naphthenics.

Physical and Chemical Properties of Mineral Oils That Affect Lubrication have been delt with by Douglas Godfrey of Herguth Laboratories, Inc. 1995 which describes viscosity as being the property of a fluid that causes it to resist flow, which mechanically is the ratio of shear stress to shear rate. Viscosity may be visualized as a result of physical interaction of molecules when subjected to flow. Lubricating oils have long chain hydrocarbon structures, and viscosity increases with chain length. Viscosity of an oil film, or a flowing column of oil, is dependent upon the strong absorption of the first layer adjacent to the solid surfaces, and the shear of adjacent layers.

Specific gravity is used which is ratio of the mass of a given volume to the mass of an equal volume of water. Therefore, specific gravity is dimensionless. The specific gravity of mineral oils also varies from 0.86 to 0.98 since the specific gravity of water is 1 at 15.6 degree C. Specific gravity decreases with increased temperature and decreases slightly as viscosity decreases for similar compositions. Reference 5 (pp. 482–484) gives the specific gravity of 81 mineral oils at 15.6 degree C.

Bulk modulus expresses the resistance of a fluid to a decrease in volume due to compression. A decrease in volume would increase density. Compressibility is the reciprocal of bulk modulus or the tendency to be compressed. Bulk modulus varies with pressure, temperature, molecular structure and gas content. Generally, mineral oils are thought to be incompressible. In high pressure hydraulic systems a high bulk modulus or low compressibility is required to transmit power efficiently and dynamically. Bulk modulus is determined by measuring the volume of an oil at various pressures or derived from density measurements at various pressures. Bulk modulus can also be measured by the speed of sound in oils under various pressures. A discussion of bulk modulus and values are given in References 9 and 10 Since a graph of pressure versus volume gives a curve, the secant to the curve is used and is called Isothermal Secant Bulk Modulus.

Gases are soluble in mineral oils to a limited amount. The amount varies with the type of gas and oil temperature. For example, 8 to 9% of air, by volume, is soluble in mineral oil at room temperature and is invisible. Dissolved gases affect oil viscosity, bulk modulus, heat transfer, oil and metal oxidation, boundary lubrication, foaming and cavitation. Boundary lubrication is improved by the oxygen in dissolved air because it continuously repairs the protective oxide films on metals. Dissolved oxygen is considered an important anti-scuff component. The amount of dissolved gas become evident when gases come out of solution vigorously when the oil is subjected to low pressures.

The amount of soluble gas is measured by ASTM D 2780 "Solubility of Fixed Gases In Liquid Test". This method physically separates the gas through an extraction process and measures the quantity volumetrically. This method allows for subsequent qualitative analysis of the extracted gas by any appropriate technique.

If the amount of a gas in oil exceeds saturation, small bubbles will form, remain suspended, and the oil will appear hazy. This is called entrained gas. The bubbles slowly rise to the surface Bubbles of a gas, such as air, in an oil film cause holes that reduce oil film continuity and decrease the film's ability to prevent solid-to-solid contact.

The relative tendency of various oils to release entrained gas is measured by a gas bubble separation method ASTM D 3427. The method uses a cylinder-like test vessel with gas inlet and outlet ports. Air, or another gas (if of interest), is introduced into the bottom of the vessel at a specified temperature and flow rate. At the end of seven minutes the gas flow is stopped and the change in density as measured by a densitometer is recorded. The test is complete when the total volume of entrained air is reduced to 0.20% by volume. The results are reported as the time it took for the oil to attain this value.

Foaming is defined as the production and coalescence of gas bubbles on a lubricant surface. Foam may be a result of a variety of problems including air leaks, contamination, and over filling of sumps. Foaming can cause loss of oil out of a vent and serious operational problems in most lubricated systems. Excessive foam can starve bearings and pumps of liquid lubricant (pump cavitation) causing failure, and cause poor performance in hydraulic systems. The foaming characteristics of an oil are measured by ASTM D-892. Using a calibrated porous stone, air is blown into the bottom of a graduated cylinder for a specified time. Immediately upon completion of the blowing period, the foam that has formed on the top of the oil is measured. Ten minutes after the completion of the blowing period, an additional measurement is made of the remaining foam as the foam retention characteristics of the oil. The results are reported in milliliters.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly (ethylene/butylene/styrene) with epoxidized polyisoprene and poly(ethylene/butylene) with epoxidized polyisoprene. Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @100° F. Viscosity), H-300E (635–690 cst @210° F. Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duroprime and Tufflo oils (6006, 6016, 6016M, 6026, 6036, 6056, 6206, etc), other white mineral oils include: Bayol, Bernol, American, Drakeol, Ervol, Gloria, Kaydol, Litetek, Lyondell (Duroprime 55, 70, 90, 200, 350, 400, Ideal FG 32, 46, 68, 100, 220, 460), Marcol, Parol, Peneteck, Primol, Protol, Sontex, and the like. Oils useful in the invention gel include: Witco 40 oil, Ervol, Benol, Blandol, Semtol-100, Semtol 85, Semtol 70, Semtol 40, Orzol, Britol, Protol, Rudol, Carnation, Klearol, 350, 100, 85, 70, 40, Pd-23, Pd 25, Pd28, FG 32, 46, 68, 100, 220, 460, Duroprime Ds-L, Ds-M, Duropac 70, 90, Crystex 22, Af-L, Af M, 6006, 6016, 6026, Tufflo 6056, Ste Oil Co, Inc: Crystal Plus 70, 200, 350, Lyondell: Duroprime DS L & M, Duropac 70, 90, Crystex 22, Crystex AF L & M, Tufflo 6006, 6016; Chevron Texaco Corp: Superta White Oil 5, Superta 7, 9, 10, 13, 18, 21, 31, 35, 38, 50, Penreco: Conosol 340, Conosol C-200, Drakeol 15, 13, 10, 10B, 9, 7, 5, 50, Peneteck Ultra Chemical Inc, Ultraol White 60Nf, Ultraol White 50Nf, Witco Hydrobrite 100, 550, 1000, and the like.

Selected amounts of one or more compatible plasticizers can be used to achieve gel rigidities of from less than about 2 gram Bloom to about 1,800 gram Bloom and higher. Tack may not completely be dependent upon the amount of the glassy phase, by using selected amount of certain low viscosity oil plasticizers, block copolymers of SEBS, SEEPS, SEPS, $SEP_n$, $SEB_n$, and the like, gel tack can be reduced or the gel can be made non-tacky.

Major or minor amounts (based on 100 parts by weight of base elastomer) of any compatible second plasticizers can be utilized in forming the invention gel, but because of the non-tack property of the invention gel, the major amount of first plasticizers used should be low viscosity plasticizers having viscosities advantageously of not greater than about 30 cSt @40° C., for example 30, 29, 28, 27, 26, 25, 24, 23, 22, 21, 20, 19, 18, 17, 16, 15, 14, 13, 12, 11, 10, 9, 8, 7, 6, 5, 4, 3 and the like. The invention gel tack decreases with decreasing oil viscosities of from about 30 to 3. Invention gels which are non-tacky to the touch can be achieved using oils with viscosities of about 10 cSt @40° C. and less. Best result can be achieved using oils with viscosities of about 6 and less. Oils of higher viscosities of from about 500 cSt @40° C. to about 30 produce higher and higher tack with increase in viscosities. Heat temperature set resistance improves with increase in oil viscosity. Oils with viscosities less than about 15 exhibit heat set at about 50° C. Therefore a combination of low viscosity oils to improve low tack and high viscosity oils to improve set can be achieved by blending various oils having the desired viscosities for the desired end use. The disassociation of polystyrene is about 100° C. to about 135° C., the invention gels do not melt below the disassociation temperature of polystyrene. It is important that fishing bait when stored in a fishing box in the hot Sun at about 50° C. to about 58° C. do not suffer substantial heat set as tested at these temperatures in a 108° U bend for one hour.

It has been found that the lower the oil viscosity, the lower the heat set of the resulting gel composition and the higher the oil viscosity use in the gel compositions of the invention, the higher the heat set of the resulting gel composition. For example, if the first plasticizer is less than about 50 SUS @100° F., the heat set of the resulting gel composition comprising 100 parts of (I) copolymers of equal parts of SEEPS 4055 and Kraton G 1651 with about 600 parts by weight of the first plasticizer, the resulting is found to have a heat set less than that of a conventional PVC plastisol fishing bait at about 50° C. However, as the 50 Vis SUS @100° F. oil of the formulation is gradually replaced with a higher viscosity oil of about 80–90 SUS @100° C., the heat set deformation improves with increasing amounts of the higher viscosity oil. In order to obtain equal heat set performance as conventional PVC plastisol fishing bait, the first and second plasticizers would have to be of equal amounts in the gel composition. Replacing the first plasticizer with a greater amount would increase the gel tack. If tack is not of great concern, then a higher amount of the second plasticizers would be beneficial for improving heat set at higher and higher temperatures to the point that the second plasticizers can reach greater than 2525 SUS @100° C. (Ideal FG 100, 220, or 460 oil) the resulting gel composition would not exhibit set at even temperatures greater than 400° F.

The cited first plasticizers with or without one or more second plasticizers can be used in sufficient amounts to achieve a gel rigidity of from about 20 gram Bloom to about 1,800 gram Bloom. The second plasticizers in effective amounts in combination with the first plasticizers can provide a greater temperature compression set than a gelatinous composition having the same rigidity formed from the first plasticizers alone. The second plasticizers when used can provide a greater temperature compression set than a gelatinous composition having the same rigidity formed from the first plasticizers alone or formed from a combination of the first plasticizers and the second plasticizers. The first plasticizers being in effective amounts with said second plasticizers can provide a Gram Tack lower than a gelatinous composition having the same rigidity formed from the second plasticizers alone.

Generally, plasticizing oils with average molecular weights less than about 200 and greater than about 700 may also be used (e.g H-300 (1290 Mn)). It is well know that minor and sufficient amounts of Vitamin E is added to the described commercially available oils during bulk processing which is useful as a oil stabilizer, antioxidant, and preservative.

Of all the factors, the amount of plasticizing oils can be controlled and adjusted advantageously to obtain substantially higher tear and tensile strength gels. The improvements in tensile strength of the invention gels are accompanied by corresponding increase in gel rigidity as the amount of plasticizing oils are lowered until the rigidity of the invention gels becomes much higher than that of the gums which surround the teeth. Although higher tensile strengths can be obtained as the amount of plasticizing oils in the gel approaches zero, the tensile strength of the floss, however, must be maintained at an acceptable gel rigidity (at sufficient high plasticizing oil levels) in order to be as soft as the gums required for flossing. For example, the rigidities of a gel containing 100, 200, or 300 parts by weight of oil is much higher than a gel containing 300, 400, 500, 600, 800, or 900 parts of oil.

These gels can exhibit a larger unit lateral contraction at the same elongation per unit of length as their counterpart parent gels from which the invention gels are derived or formed. This property would allow a same unit volume of gel when elongated as its parent to easily wedge between the teeth when flossing. It would seem that a gel having the 10 $cm^3$ volume made from a ratio of 100 parts by weight of copolymer and 400 parts plasticizer would have a unique macro volume configurations that is at equilibrium with the plasticizer which is much like a 3-D fingerprint which is uniquely different from any other gel of a different copolymer to plasticizer ratio. Reducing the plasticizer content of a ratio 100:400 gel to a 100:300 ratio of copolymer to plasticizer will decrease the amount of plasticizer, but the original macro volume configurations will remain the same.

Speculative theories not withstanding, configurations may take the form of (1) swiss cheese, (2) sponge, (3) the insides of a loaf of bread, (4) structures liken to ocean brain corals, (5) large structures and small structures forming the 3-D gel volume landscape, (6) the outer heated surface which cools faster than the inner volumes of the gel during its cooling histories may have a patterned crust (rich in A micro-phases) like that of a loaf of bread and the inner volume may have much like 1–5, and (7) the many different possible structures are unlimited and volume landscapes may be interconnected at the macro-level by threads or micro-strands of Z micro-phases.

The amount of plasticizer extracted can advantageously range from less than about 10% by weight to about 90% and higher of the total weight of the plasticizer. More advantageously, the extracted amounts of plasticizer can range from less than about 20% by weight to about 80% by weight of the total plasticizer, and still more advantageously, from about 25% to about 75%. Plasticizing oils contained in the invention gels can be extracted by any conventional methods, such as solvent extraction, physical extraction, pressure, pressure-heat, heat-solvent, pressure-solvent-heat, vacuum extraction, vacuum-heat extraction, vacuum pressure extraction, vacuum-heat-pressure extraction, vacuum-solvent extraction, vacuum-heat-solvent-pressure extraction, etc. The solvents selected, should be solvents which do not substantially disrupt the A and Z phases of the (I) copolymers forming the invention gels. Any solvent which will extract plasticizer from the gel and do not disrupt the A and Z phases can be utilized Suitable solvents include alcohols, primary, secondary and tertiary alcohols, glycols, etc., examples include methanol, ethanol, tetradecanol, etc. Likewise, the pressures and heat applied to remove the desired amounts of oils should not be sufficient to disrupt the A and Z domains of the (I) copolymers. To form a lower rigidity gel, the simplest method is to subject the gel to heat in a partial vacuum or under higher vacuum for a selected period of time, depending on the amount of plasticizer to be extracted.

Surprisingly, as disclosed in my application Ser. No. 09/896,047 filed Jun. 30, 2001, oil extraction from the invention gels can be achieved with little or no energy in the presence of one or more silicone fluids to almost any degree. A theory can be made to explain the physics involved in the extraction process which reasoning is as follows: (1) When water is placed in contact with an oil extended gel, the gel will not over time exhibit weight loss (2) When oil is add to a column of water in a test tube, the oil will separate out and find its level above the column of water. (3) The surface tension of water at 25° C. is about 72.0 mN/m. (4) The surface tension of oil (mineral oil) at 25° C. is about 29.7 mN/m. (5) The surface tension of silicone fluid at 25° C. range from abut 16 to abut 22 mN/m (for example: the surface tension of 100 cSt silicone fluid at STP is 20.9 mN/m). (6) The density of oil is less than the density of silicone fluid, silicone grease, silicone gel, and silicone elastomer. (7) Oil is not a polar liquid and is highly compatible with the rubber phase of the oil gel forming polymer. (8) Silicone is polar and not compatible with the polymer's rubber phase.

The molecules of a liquid oil drop attract each other. The interactions of an oil molecule in the liquid oil drop are balanced by an equal attractive force in all directions. Oil molecules on the surface of the liquid oil drop experience an imbalance of forces at the interface with air. The effect is the presence of free energy at the surface. This excess energy is called surface free energy and is quantified as a measurement of energy/area. This can be described as tension or surface tension which is quantified as a force/length measurement or m/Nm.

Clearly gravity is the only force pulling on the extracted oil from the gel in the presence of silicone fluid at the gel-petri dish interface in the examples below. In the case of gel samples in the petri dishes in contact with silicone fluids, the extracted oil are collected on the top surface layer of the silicone fluid while the silicone fluid maintain constant contact and surrounds the gel sample. In the case of gel placed in a test tube of silicone fluid of different viscosity, the oil is extracted and migrates and collect at the top of the silicone fluid surface while the gel reduces in volume with time. The oil extraction process in silicone is accompanied by buoyant forces removing the extracted oil from the surroundings of the gel constantly surrounding the gel with fresh silicone fluid while in the example of alcohol, since the oil is heavier, the oil is maintained and surrounds the gel sample forming a equilibrium condition of oil surround the gel sample while keeping the alcohol from being in contact with the gel sample. Therefore in order to use alcohol to extract oil from a gel sample, the extracted oil must be constantly removed from the oil alcohol mixture as is the case during soxhlet extraction which process requires additional energy to pump the oil-alcohol mixture away from the sample and removing the oil before forcing the alcohol back to the gel sample surface to perform further extraction.

Silicone fluid is efficient and useful for extracting oil form oil gel compositions with the assistance of gravity and buoyancy of oil in the silicone fluids.

It is very difficult to extract, separate, or remove oil from an oil gel composition by positive or vacuum pressure or heat while using little or no energy and because of the affinity of the rubber midblock for oil, not even the weight of a two ton truck resting on a four square foot area (placing a layer of gel between four pairs of one foot square parallel steel plates one set under each of the truck tire resting on the gels) can separate the oil from the gel composition.

The use of silicone fluids of various viscosity acts as a liquid semi porous membrane when placed in constant contact with an oil gel composition will induce oil to migrate out of the gel composition. By the use of gravity or oil buoyancy, no energy is required run the oil extraction process.

In the case of the invention gels of this application made in the shape of a fishing bait in contact with silicone fluid, the elastomer or rubber being highly compatible with the oil, holds the oil in place within the boundary of the rubber molecular phase. It is this affinity of the (i) rubber and oil molecules and (ii) the attraction of oil molecules for each other that prevents the oil from bleeding out of the surface of the gel body. There exist then, at the surface of the gel several types of surface tensions of: (iii) oil-air surface tension, (iv) oil-rubber surface tension, (v) rubber-air surface tension, (vi) rubber/oil-air surface tension, and (vii) rubber-rubber surface tension. Other forces acting on the gel are: the elastic force of the polymer network pulling inwards, similar to stretched out rubber bands, which is in equilibrium with the oil molecules' attraction to the rubber molecules of the polymer network. In the case of SBS, the lower compatibility of the midblock butadiene with oil, once a gel is made, the SBS network immediately contracts due to elastic forces to produce oil bleeding which is evidence of the poor compatibility of the rubber block for the oil molecules.

The intermolecular forces that bind similar molecules together are called cohesive forces. Intermolecular forces that bind a substance to a surface are called adhesive forces.

When two liquids are in contact such as oil and silicone fluid, there is interfacial tension. The more dense fluid is referred to herein as the "heavy phase" and the less dense fluid is referred to as the "light phase". The action at the surface of the oil extended polymer gel surface when brought into contact with silicone fluid is as follows: a drop of silicone fluid when placed on the flat surface of a oil extended polymer gel will wet the gel surface and spread over a larger area as compared to a drop of oil placed on the same gel surface. Because the surface free energy of the silicone fluid in contact with the gel surface is lower than the surface free energy of the oil, the silicone fluid has the ability to displaces the oil from the surface of the gel.

The invention gels can optionally comprise selected major or minor amounts of one or more polymers or copolymers (III) provided the amounts and combinations are selected without substantially decreasing the desired properties. The polymers and copolymers can be linear, star-shaped, branched, or multiarm; these including: (SBS) styrene-butadiene-styrene block copolymers, (SIS) styrene-isoprene-styrene block copolymers, (low styrene content SEBS such as Kraton 1650 and 1652) styrene-ethylene-butylene-styrene block copolymers, (SEP) styrene-ethylene-propylene block copolymers, (SEPS Kraton RP-1618) styrene-ethylene-propylene-styrene block copolymers, $(SB)_n$, styrene-butadiene and $(SEB)_n$, $(SEBS)_n$, $(SEP)_n$, $(SI)_n$ styrene-isoprene multi-arm, branched or star-shaped copolymers, polyethyleneoxide (EO), poly(dimethylphenylene oxide) and the like. Still, other (III) polymers include homopolymers which can be utilized in minor amounts; these include: polystyrene, polybutylene, polyethylene, polypropylene and the like.

In the case of high molecular weight and combination of high styrene content of the block copolymer which may be the reason for improve tear and fatigue resistance, these properties may be achieved and maintained by blending (I) copolymers of SEEPS with (III) copolymers of SBS (Kraton D 1101, 1144, 1116, 1118, 4141, 4150, 1133, 1184, 4158, 1401P, 4240, and KX219), SEBS (G1651, 1654).

Other (III) polymers useful in the invention gels include: of trifluoromethyl-4,5-difuoro-1,3-dioxole and tetrafluoroethylene, polytetrafluoroethylene, maleated poly(styrene-ethylene-butylene), maleated poly(styrene-ethylene-butylene)n, maleated poly(styrene-ethylene-butylene-styrene), maleated poly(styrene-ethylene-propylene)n, maleated poly(styrene-ethylene-propylene-styrene), poly(dimethylphenylene oxide), poly(ethylene-butylene), poly(ethylene-propylene), poly(ethylene-styrene) interpolymer made by metallocene catalysts, using single site, constrained geometry addition polymerization catalysts, poly(styrene-butadiene), poly(styrene-butadiene)n, poly(styrene-butadiene-styrene), poly(styrene-ethylene-butylene), poly(styrene-ethylene-butylene)n, poly(styrene-ethylene-butylene-styrene), poly(styrene-ethylene-butylene-styrene), poly(styrene-ethylene-propylene), poly(styrene-ethylene-propylene)n, poly(styrene-ethylene-propylene-styrene), poly(styrene-isoprene), poly(styrene-isoprene)n, poly(styrene-isoprene-styrene), poly(styrene-isoprene-styrene)n, polyamide, polybutylene, polybutylene, polycarbonate, polydimethylsiloxane; polyethylene vinyl alcohol copolymer, polyethylene, polyethyleneoxide, polypropylene, polystyrene, polyvinyl alcohol, wherein said selected copolymer is a linear, radial, star-shaped, branched or multiarm copolymer, wherein n is greater than one When the selected (III) polymers and copolymers contain greater glassy block of styrene content of 33 and higher, such may be effective to provide a Gram Tack lower than a gelatinous composition having the same rigidity formed from the (I) block copolymers and corresponding first plasticizers alone or the first plasticizers with a second plasticizers. The selected component (III) polymers of polystyrene forming a styrene content of 33 and higher when used in effective amounts may provide a greater temperature compression set than a gelatinous composition having the same rigidity formed from the (I) block copolymers and corresponding first plasticizers alone or the first plasticizers with a second plasticizer.

On the other hand, the lower viscosity first plasticizer can impart lower Gram Tack to the invention gels than an increase of styrene content of the (I) copolymers or (III) polymers and copolymers. The low tack and non tacky invention gels can be made from one or more linear, branched, star-shaped (radial), or multiarm block copolymers or mixtures of two or more such block copolymers having one or more midblock polymer chains which invention gels have use as articles with high tear propagation resistance. The invention gels also possess high tensile strength and rapid return from high extension and can exist in an altered state of delay elastomeric recovery as it regains its original shape following high extensions or dynamic deformations. The invention gels also exhibit low set, high dimensional stability, crack, tear, craze, and creep resistance, excellent tensile strength and high elongation, long service life under shear, stress and strain and capable of withstanding repeated dynamic shear, tear and stress forces, excellent processing ability for cast molding, extruding, fiber forming film forming and spinning, non-toxic, nearly tasteless and odorless, soft and strong, optically clear, highly flexible, possessing elastic memory, substantially with little or no plasticizer bleedout, and having low or no tack in contact with human hand which reduction in tackiness can be measured. The non tacky and optical properties of the invention gels do not rely on powders or surface activation by additives to establish their non-tackiness. The invention gels' non-tackiness pervasive the gels' entire bulk or volume. No matter how deep or in which direction a cut is made, the invention gels are non tacky throughout (at all points internally as well as on the gels' surface). Once the gel is cut, the invention gel immediately exhibits non-tackiness at its newly cut surface. Hence, the homogeneity of the non-tackiness and optical properties of the invention gels are not known.

Example of (III) polymers, copolymers, and blends include: (a) Kraton G 1651, G 1654X; (b) Kraton G 4600; (c) Kraton G 4609; other suitable high viscosity polymer and oil s include: (d) Tuftec H 1051; (e) Tuftec H 1041; (f) Tuftec H 1052; (g) low viscosity Kuraray SEEPS 4033 (hydrogenated styrene isoprene/butadiene block copolymers, more specifically, hydrogenated styrene block polymer with 2-methyl-1,3-butadiene and 1,3-butadiene); (h) Kuraray SEBS 8006; (i) Kuraray SEPS 2005; (j) Kuraray SEPS 2006, and (k) blends (polyblends) of (a)–(h) with other polymers and copolymers include: (1) SEBS-SBS; (2) SEBS-SIS; (3) SEBS-(SEP); (4) SEBS-$(SEB)_n$; (5) SEBS-$(SEB)_n$; (6) SEBS-$(SEP)_n$; (7) SEBS-$(SI)_n$; (8) SEBS-(SI) multiarm; (9) SEBS-$(SEB)_n$; (10) $(SEB)_n$ star-shaped copolymer; (11) s made from blends of (a)–(k) with other homopolymers include. (12) SEBS/polystyrene; (13) SEBS/polybutylene; (14) SEBS/polyethylene; (14) SEBS/polypropylene; (16) SEP/SEBS, (17) SEP/SEPS, (18) SEP/SEPS/SEB, (19), SEPS/SEBS/SEP, (20), SEB/SEBS (21), EB-EP/SEBS (22), SEBS/EB (23), SEBS/EP (24), (25) $(SEB)_n$ s, (26) $(SEP)_n$, (27) Kuraray 2007 (SEPS), (28) Kuraray 2002, (SEPS), and the like.

Representative examples of commercial elastomers that can be combined with the multiblock and star-shaped copolymers (III) described above include: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, G1730

(SEPSEP), FG1901X and FG1921X. Kuraray's SEPS, SEP/SEPS or SEP/SEB/SEPS Nos. SEP 1001, SEP 1050, 2027, 2003, SEPS 2006, SEPS 2023, SEPS 2043, SEPS 2063, SEPS 2050, SEPS 2103, SEPS 2104, SEPS 2105, SEBS 8004, SEBS 8007, H-VS-3 (S-V-EP-S) and the like. Dow poly(ethylene-styrene) random copolymers (interpolymers) produced by metallocene catalysts, using single site, constrained geometry addition polymerization catalysts resulting in poly(ethylene-styrene) substantially random copolymers such as ESI-#1 thru #38, including ES16, ES24, ES27, ES28, ES28, ES30, ES44 with styrene wt % of 15.7, 23.7, 27.3, 28.1, 39.6 & 43.9 respectively, M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively), S copolymers (ES72, ES73, and ES74 with styrene wt % of 72.7, 72.8, and 74.3 respectively). Other grade copolymers include ES60 (melt index 0.1, 0.5, 3, 10), ES20 (MI=0.1. 0.5, 3, 11).

The Brookfield Viscosity of a 5 weight percent solids solution in toluene at 30° C. of 2006 is about 27. Typical Brookfield Viscosities of a 10 weight percent solids solution in toluene at 30° C. of Kuraray SEP 1001, SEP 1050, SEPS 2007 SEPS 2063, SEPS 2043, SEPS 2005, SEPS 2006, are about 70, 70, 17, 29, 32, 50, 1200, and 1220 respectively Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively. Other polymers such as, thermoplastic crystalline polyurethane copolymers with hydrocarbon midblocks can also be employed.

The glassy A component type homopolymers can be advantageously added to provide non-tackiness which are selected from one or more homopolymers of: polystyrene, poly(alpha-methylstyrene), poly(o-methylstyrene), poly(m-methylstryene), poly(p-methylstyrene), and poly (dimethylphenylene oxide) (GE PPO 612 and Arizona XR 6504). Such glassy polymers can be use in forming the invention gel, but would increase hot tack.

The average molecular weight of the glassy homopolymers useful in the invention gels advantageously can range from about 2,500 to about 90,000, typical about 3,000, 4,000, 5,000, 6,000; 7,000; 8,000; 9,000; 10,000; 11,000; 12,000, 13,000, 14,000; 15,000; 16,000; 17,000; 18,000; 19,000, 20,000; 30,000; 40,000; 50,000; 60,000; 70,000; 80,000; 90,000 and the like. Example of various molecular weights of commercially available polystyrene: Aldrich Nos.: 32,771-9 (2,500$M_w$), 32,772-7 (4,000 Mw), 37,951-4 (13,000 Mw), 32-774-3 (20,000 Mw), 32,775-1 (35,000 Mw), 33,034-5 (50,000 Mw), 32,777-8 (90,000 Mw); poly (alpha-methylstyrene) #41,794-7 (1,300 Mw), 19,184-1 (4,000 Mw); poly(4-methylstyrene) #18,227-3 (72,000 Mw), Endex 155, 160, Kristalex 120, 140 from Hercules Chemical, GE: Blendex HPP820, HPP822, HPP823, and the like.

Microspheres suitable for use include expanded or unexpanded DE (091-80) phenolic microspheres from Expandcel, Inc. U.S. Especially DE 091-80 can be compounded into a masterbatch with polyvinylaciate, polyvinylethylaciate, polyethylevinylaciate, polymethylaciate, and the like in high concentrations to form strands, pelets, and shapes of any kind which can be configured into regular or irrgular assemblies such as a network, web, lattices and molded with high temperature molten gel thereby expanding the network, web, lattices, and assemblies of compounded shapes of masterbatch of expandcel so as to expand in place the preselected and pre-assebled shaped of expandable foam. In this way, in place foam of any shape and kind are formed in place within the invention gel or on the surface of the invention gel and the like.

Suitable triblock copolymers (III) and their typical viscosities are further described: styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Shell Technical Bulletin SC: 1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68-79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity SEBS triblock copolymers includes Kuraray's SEBS 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of SEBS, SEPS, $(SEB)_n$, $(SEP)_n$ polymers can also be utilized in the present invention provided such polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's SEBS polymer 8006 the S:EB weight ratio is about 35:65. In the case of Kurary's 2005 (SEPS), and 2006 (SEPS), S:EP weight ratios are 20:80 and 35:65 respectively. Much like S:EB ratios of SEBS and $(SEB)_n$, the SEP ratios of very high viscosity SEPS triblock copolymers are about the same and can typically vary as broadly.

The triblock copolymers (III) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

The high glassy component copolymers suitable for use in forming the invention gel include high styrene component BASF's Styroflex senes copolymers including BX 6105 with a statistical SB sequence for the low elastomeric segments (styrene to butadiene ratio of 1:1) and an overall styrene content of almost 70%, high styrene content Shell Kraton G, Kraton D-1122X (SB)n, D-4122 SBS, D-4240 (SB)n, D-4230 (SB)n, DX-1150 SBS, D-4140 SBS, D-1115 SBS, D-4222 SBS, Kraton D-1401P, SEBS, Dexco's Vector 6241-D, 4411-D, Fina's Finaclear high styrene content SBS series copolymers, Phillips Petroleum's XK40 K-Resin styrene/butadiene copolymers, Kuraray's S2104 SEPS The copolymers include amorphous polymers with high styrene content: SBS, SIS, SEPS, SEB/EPS, and the like. The copolymers with glassy to elastomeric ratios can range from 37:63, 37.6:62.4, 38:62, 39:61, 40:60, 41:59, 42:58, 43:57, 44:65, 45:55, 46.54, 47.53, 48.52, 49:51, 50:50, 51:49, 52:48, 53:47, 54:46, 55:45, 56:44, 57:43, 58:42, 59:41, 60:40, 6:39, 62:38, 63:37, 64:36, 65:35, 66:34, 67:33, 68.32, 69:31, 70:30, 7:29, 72:28, 73:27, 74:26, 75:25, 76:24, 77:23, 78:22, 79:21, to 80:20 and higher. High styrene content Dow ES30, and ES44 with styrene wt % of 15.7 23.7, 27.3, 28.1, 39.6 & 43.9 respectively, M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively, S copolymers ES72, ES73, and ES74 with styrene wt % of 72.7, 72.8, and 74.3 respectively may also be used. These hard to process polymers can be added (from 0.01 to 30 parts by weight) by dry blending in combination with 200–400 parts oil and with SEEPS 4055, 4033, 4077, 4045 and the like and extruded at about between 75° C.–135° C. to form a pre-blend and then formulated with additional oil or/or oil and (I) copolymers to produce the final invention gel.

Suitable polyolefins include polyethylene and polyethylene copolymers such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141-XT, 1430, 1420, 1320, 3330, 3150, 2912, 3340, 3460; Dow Attane (ultra low density ethylene-octene-1 copolymers) 4803, 4801, 4602, Eastman Mxsten CV copolymers of ethylene and hexene (0.905–0.910 g/cm3).

On the other hand, the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F. ).

The incorporation of such adhesion resins is to provide strong and dimensional stable adherent invention gels, gel composites, and gel articles. Typically such adherent invention gels can be characterized as adhesive invention gels, soft adhesives or adhesive sealants. Strong and tear resistant adherent invention gels may be formed with various combinations of substrates or adhere (attach, cling, fasten, hold, stick) to substrates to form adherent gel/substrate articles and composites.

The present invention gel can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the gel of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl- pentaeythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), Tinuvin P, 123, 144, 213, 234, 326, 327, 328, 571, 622, 770, 765, Chimassorb 119, 944, 2020, Uvitex OB, Irganox 245, 1076, 1098, 1135, 5057, HP series: 2215, 2225, 2921, 2411, 136, stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe3O4, —Fe2O3, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass, microspheres, barium ferrite, wollastonite and the like. The report of the committee on Magnetic Materials, Publication NMAB-426, National Academy Press (1985) is incorporated herein by reference.

Various glassy phase associating resins having softening points above about 120° C. can also serve as additives to increase the glassy phase of the Invention gel and met the non-tackiness criteria, these include: Hydrogenated aromatic resins (Regalrez 1126, 1128, 1139, 3102, 5095, and 6108), hydrogenated mixed aromatic resins (Regalite R125), and other aromatic resin (Picco 5130, 5140, 9140, Cumar LX509, Cumar 130, Lx-1035) and the like.

The commercial resins which can aid in adhesion to materials (plastics, glass, and metals) may be added in minor amounts to the invention gels, these resins include: polymerized mixed olefins (Super Sta-tac, Betaprene Nevtac, Escorez, Hercotac, Wingtack, Piccotac), polyterpene (Zonarez, Nirez, Piccolyte, Sylvatac), glycerol ester of rosin (Foral), pentaerythritol ester of rosin (Pentalyn), saturated alicyclic hydrocarbon (Arkon P), coumarone indene, hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035), and the like.

In my U.S. Pat. No. 5,760,117, is described a non-adhering gel which is made non-adhearing, by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. Such non-adhering gels by including additives are no longer optical clear and with time some of the additives blooms uncontrollably to the gel surface.

The invention gels are also suitable for forming composites combinations with various substrates. The substrate materials are selected from the group consisting of paper, foam, plastic, fabric, metal, metal foil, concrete, wood, glass, various natural and synthetic fibers, including glass fibers, ceramics, synthetic resin, and refractory materials.

The invention gels can also be made into composites. The invention gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten gel composition is deformed as it is being cooled. Useful open-cell plastics include. polyamides, polyimides, polyesters, polyisocyanurates, polyisocyanates, polyurethanes, poly (vinyl alcohol), etc. Open-celled Plastic (sponges) suitable for use with the compositions are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The invention gels denoted as "G" can be physically interlocked with a selected material denoted as "M" to form composites as denoted for simplicity by their combinations $G_nG_n$, $G_nM_n$, $G_nM_nG_n$, $M_nG_nM_n$, $M_nG_nG_n$, $G_nG_nM_n$, $M_nM_nG_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, and the like or any of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from less than about 2 gram to about 1,800 gram Bloom and higher).

Furthermore, the interlocking materials with the gel of the invention may be made from flexible materials, such as fibers and fabrics of cotton, flax, and silk. Other flexible materials include: elastomers, fiber-reinforced composites, mohair, and wool. Useful synthetic fibers include acetate, acrylic, aremid, glass, modacrylic polyethylene, nylon, olefin, polyester, rayon, spandex, carbon, sufar, polybenzimidazole, and combinations of the above. Useful open-cell plastics include: polyamides, polyimides, polyesters, polyisocyanurates, polyisocyanates, polyurethanes, poly(vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference. These include: open and non-opened cell silicone, polyurethane, polyethylene, neoprene, polyvinyl chloride, polyimide, metal, ceramic, polyether, polyester, polystyrene, polypropylene. Example of such foams are: Thanol®, Arcol®, Ugipol®, Arcel®, Arpak®, Arpro®, Arsan®, Dylite®, Dytherm®, Styrofoam®, Trymer®, Dow Ethafoam®, Ensolite®, Scotfoam®, Pyrell®, Volana®, Trocellen®, Minicel®, and the like.

Sandwiches of gel-material (i.e. gel-material-gel or material-gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the invention gels are superior in performance to triblock copolymer gels which are much less resistance to crack propagation caused by long term continue dynamic loadings.

Adhesion to substrates is most desirable when it is necessary to apply the adherent invention gels to substrates in the absence of heat or on to a low temperature melting point substrate for later peel off after use, such as for sound damping of a adherent gel composite applied to a first surface and later removed for use on a second surface. The low melting substrate materials which can not be exposed to the high heat of the molten adherent invention gels, such as low melting metals, low melting plastics (polyethylene, PVC, PVE, PVA, and the like) can only be formed by applying the adherent invention gels to the temperature sensitive substrates. Other low melting plastics include: polyolefins such as polyethylene, polyethylene copolymers, ethylene alpha-olefin resin, ultra low density ethylene-octene-1 copolymers, copolymers of ethylene and hexene, polypropylene, and etc. Other cold applied adherent gels to teflon type polymers: TFE, PTFE, PEA, FEP, etc., polysiloxane as substrates are achieved using the adherent invention gel.

Likewise, adherent gel substrate composites can be both formed by casting hot onto a substrate and then after cooling adhering the opposite side of the adherent gel to a substrate having a low melting point. The adherent gel is most essential when it is not possible to introduce heat in an heat sensitive or explosive environment or in outer space. The use of solid or liquid resins promotes adherent gel adhesion to various substrates both while the adherent gel is applied hot or at room temperature or below or even under water. The adherent invention gels can be applied without heating to paper, foam, plastic, fabric, metal, concrete, wood, wire screen, refractory material, glass, synthetic resin, synthetic fibers, and the like.

The adhesion properties of the invention gels are determined by measuring comparable rolling ball tack distance "D" in cm using a standard diameter "d" in mm stainless steel ball rolling off an inclined of height "H" in cm. Adhesion can also be measured by determining the average force required to perform 180° C. peel of a heat formed $G_1M_1$ one inch width sample applied at room temperature to a substrate $M_2$ to form the composite $M_1G_1M_2$. The peel at a selected standard rate cross-head separation speed of 25 cm/minute at room temperature is initiated at the $G_1M_2$ interface of the $M_1G_1M_2$ composite, where the substrate $M_2$ can be any of the substrates mentioned and $M_1$ preferably a flexible fabric.

Glassy phase associating homopolymers such as polystyrene and aromatic resins having low molecular weights of from about 2,500 to about 90,000 can be blended with the triblock copolymers of the invention in large amounts with or without the addition of plasticizer to provide a copolymer-resin alloy of high impact strengths. More advantageously, when blended with multiblock copolymers and substantially random copolymers the impact strengths can be even higher. The impact strength of blends of from about 150 to about 1,500 parts by weight glass phase associating polymer and resins to 100 parts by weight of one or more multiblock copolymers can provide impact strength approaching those of soft metals. At the higher loadings, the impact strength approaches that of polycarbonates of about 12 ft-lb/in notch and higher.

The invention gel are non tacky to the touch and can be quantified using a simple test by taking a freshly cut Gel probe of a selected gel rigidity made from the invention gel. The gel probe is a substantially uniform cylindrical shape of length "L" of at least about 3.0 cm formed components (1)–(3) of the invention gel in a 16×150 mm test tube. The gel probe so formed has a 16 mm diameter hemi-spherical tip which (not unlike the shape of a human finger tip) is brought into perpendicular contact about substantially the center of the top cover of a new, un-touched polystyrene reference surface (for example the top cover surface of a sterile polystyrene petri dish) having a diameter of 100 mm and a weight of 7.6 gram resting on its thin circular edge (which minimizes the vacuum or partial pressure effects of one flat surface in contact with another flat surface) on the flat surface of a scale which scale is tared to zero. The probe's hemi-spherical tip is place in contact with the center of the top of the petri dish cover surface and allowed to remain in contact by the weight of the gel probe while held in the upright position and then lifted up. Observation is made regarding the probe's tackiness with respect to the clean reference polystyrene surface. For purpose of the foregoing reference tack test, tackiness level 0 means the polystyrene dish cover is not lifted from the scale by the probe and the scale shows substantially an equal positive weight and negative weight swings before settling again back to zero with the swing indicated in (negative) grams being less than 1.0 gram. A tackiness level of one 1, means a negative swing of greater than 1.0 gram but less than 2.0 gram, tackiness level 2, means a negative swing of greater than 2 gram but less than 3 gram, tackiness level 3, means a negative swing of greater than 3 gram but less than 4 gram, before settling back to the zero tared position or reading. Likewise, when the negative weight swing of the scale is greater than the weight of the dish (i.e., for the example referred above, greater than 7.6 gram), then the scale should correctly read −7.6 gram which indicates the dish has completely been lifted off the surface of the scale. Such an event would demonstrate the tackiness of a gel probe having sufficient tack on the probe surface. The invention gel fails to lift off the polystyrene reference from the surface of the scale when subject to the foregoing reference tack test. Advantageously, the invention gel can register a tackiness level of less than 5, more advantageously, less than 3, still more advantageously, less than 2, and still more advantageously less than 1. The non-tackiness of the invention gel can advantageously range from less than 6 to less than 0.5 grams, typical tack levels are less than 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5, 2.8, 3.0, 3.5, 4.0, 4.5, 5.0 grams and the like. Whereas probes of gels made from amorphous gels such as SEPS, SEBS, S-EP-EB-S, and the like with copolymer styrene to rubber ratio of less than 37.63 and plasticizer of higher than 30 cSt 40° C. are found to lift the polystyrene reference from the surface of the scale. For purposes of indicating tack, the method above can provide gel tack level readings of 1, 2, 3, 4, 5, 6, and 7 grams. More accurate and sensitive readings can be made using electronic scales of tack levels of less than 1 gram. By this simple method tack levels (of a gel probe on a polystyrene reference surface) can be measure in terms of gram weight displacement of a scale initially tared to zero. For purpose of the present invention the method of using a polystyrene reference surface having a weight of 7.6 grams in contact and being lifted by the tackiness of a cylindrical gel probe having a 16 mm diameter hemi-spherical tip is used to determine the tackiness of the invention gel. The level of tack being measured in gram Tack at 23° C.

Non tacky is defined for the purpose of the invention gel as the feeling registered in the mind by the sense of touch of the fingers of the human hand. An reinforcing observation is that a non tacky reference gel sample does not cling or stick to the fingers under its own weight when the force of holding the reference gel sample between the fingers is released and the sample is allowed to fall by the action of gravity. A simple way to accurately measure the non tacky feeling as sensed by the fingers is to drop a reference gel sample having a cylindrical shape of about 1.0 cm diameter and 1.0 cm in length a distance of 10 cm on to the surface of a polystyrene petri dish having a diameter of 10 cm inclined at 45°. The reference gel sample is considered non tacky if it (1) "bounce at least twice before coming to rest", (2) "bounce off", (3) "bounce and then rolls off", or (4) "rolls off" on striking the polystrene surface. If none of (1) thru (4) is observed, then the level of Gram Tack can be determined by the gel sample method above.

The invention gel can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

The invention gels are prepared by blending together the components (I, II, or III) including the various additives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (III) used. These components blend easily in the melt and a heated vessel equipped with a stirrer is all that is required Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The invention gel can also contain gases as an additive, i.e. the gel can be foamed. Foam is herein defined as tightly or loosely packing aggregation of gas bubbles, separated from each other by thin or thick layers of gel. Many types of foamed invention gels (from ultra high density to ultra low density) can be produced as desired by (i) adding gas to the molten gel during processing, and (ii) producing gas in the molten get during processing. Gas can be added by whipping a gas into the molten gel before it cools or introduce a gas into the molten gel and then expand or reduce the size of the gas bubbles by reducing the pressure to reduce the bubbles size or applying high pressure to expand the bubbles size. In this regard, inert gases such as Carbon dioxide, Nitrogen, Helium, Neon, Argon, Krypton, Xenon and Radon are suitable. Air can also be used. Gas can be produced in the molten gel by adding one or more of a "blowing agent" to the Useful blowing agents include dinitroso compounds, such as dinitroso pentamethylenetetramine, azodicarbonamide, 4,4'oxybis(benzenesulfonyl) hydrazine, 5-phenyltetrazole, p-toluenesulfonyl semicarbazide, sulfonyl hydrazide, such as benzene sulfonylhydrazide. Water can be used as a "blowing agent" to [1] produce varying density of foam invention gels; water used to advantage can be in the form of mist, droplets, steam, and hot or cold water. The density of the foam invention gels can vary from less than 1.00 kilograms per cubic meter to near the solid gel density. Although the materials forming soft solid invention gels may be more shear resistant, the same materials when made into a foam become much less shear resistant.

The gel articles can be formed by blending, injection molding, extruding, spinning, casting and other conventional methods. For example, Shapes having various cross-section can be extruded using a HP-2000 Mixing extruder from Dek-tron Scientific Instruments of Plainfield, N.J. 07060, USA.

In general, the basis of this invention resides in the fact that one or more of a high viscosity linear multiblock and star-shaped multiblock copolymers (I) or a mixture of two or more of such copolymers having (A) end block to elastomeric block ratio preferably within the contemplated range of styrene to rubber ratios of from about 20:80 to about 40:60 and higher, more preferably from between about 31:69 to about 40:60 and higher when blended in the melt with an appropriate amount of plasticizing oil makes possible the attainment of invention gels having a desirable combination of physical and mechanical properties, notably high elongation at break of at least 1,600%, ultimate tensile strength of about $8 \times 10^5$ dyne/cm$^2$ and higher, low elongation set at break of substantially not greater than about 2%, tear resistance of $5 \times 10^5$ dyne/cm$^2$ and higher, substantially about 100% snap back when extended to 1,200% elongation.

More specifically, the invention gels of the present invention exhibit one or more of the following properties. These are: (1) tensile strength of about $8 \times 10^5$ dyne/cm$^2$ to about $10^7$ dyne/cm$^2$ and greater; (2) elongation of less than 1,600% to about 3,000% and higher, (3) elasticity modulus of about $10^4$ dyne/cm$^2$ to about $10^6$ dyne/cm$^2$ and greater, (4) shear modulus of about $10^4$ dyne/cm$^2$ to about $10^6$ dyne/cm$^2$ and greater as measured with a 1, 2, and 3 kilogram load at 23° C.; (5) gel rigidity of about less than about 2 gram Bloom to about 1,800 gram Bloom and higher; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

As the invention gels formed from multiblock copolymers (I) having more and more midblock polymer chains can be expected to exhibit greater delay recovery form extension or longer relaxation times with increasing number of midblocks and increasing midblock lengths, such invention gels having more than three midblocks forming the copolymers (I) can exhibit extreme tear resistance and excellent tensile strength while at the same time exhibit almost liquid like properties. For example, a fun toy can be made from (S-E-EB-E-S), (S-B-EB-EB-S), (S-E-EP-E-EP-S), (S-P-EB-P-EB-S), (S-E-EB-E-EB-E-S), (S-E-EP-E-EP-E-EP-E-S), (S-E-EP-EP)$_n$, (S-B-EP-E-EP)$_n$, (S-E-EP-E-EP-E)$_n$, (S-E-EB-E-EB-E-EB-E-EB-S)$_n$ copolymer invention gels which are molded into cube shapes when placed on the surface of a incline will collect it self together and flow down the incline as a moving body much like a volume of water moving on a high surface tension surface. This is due to the greater distance between the end block (A) domains. Such liquid like performing invention gels can be very strong and exhibit extreme tear resistance as exhibited by invention gels made from (S-E-EP-S) multiblock copolymer invention gels with shorter (A) distance between domains. Such liquid like invention gels when shaped into a cube will be deformed by the force of gravity on Earth, but will retain its memory and regain to its molded cube shape when released in outer space or reform into a cube if let loose in a container of liquid of equal density. As a comparison, such a toy formed in the shape of a large cube from a high viscosity triblock copolymer with a plasticizer content of 1:1,600 parts will be flattened by the force of gravity and run down an incline, but is very fragile and will start to tear if attempt is made to pick it up by hand. This is an excellent comparison of the difference of tear resistance difference between triblock copolymer gels and multiblock copolymer invention gels. A useful application is to use such an elastic liquid gel volume to fill a container or to encapsulate an electrical or electronic component in a container filling every available space, when needed, the shapeless gel volume can be removed by pouring it out of the container whole.

The most surprising, unexpected, versatile use of the composition is dental flossing. The dental floss can be almost any shape so long as it is suitable for dental flossing. A thick shaped piece of the composition can be stretched into a thin shape and used for flossing. A thinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the gel resist tearing, shearing, and crazing while being stretched to a high degree in such situations. For example, dental gel floss can take the form of a disk where the segments of the circumference of the disk is stretched for flossing between the teeth. Other shaped articles suitable for flossing include threads, strips, yarns, tapes, etc., mentioned above.

In order for invention gels to be useful as a dental floss, it must overcome the difficult barriers of high shearing and high tearing under extreme elongation and tension loads. The difficulties that the invention gels must overcome during flossing can be viewed as follows: during the action of flossing, the gel is stretched from no less than about 200% to about 1,100% or higher, the gel floss is deformed as it is pulled down with tearing action between the contacting surfaces of the teeth, then, the wedge of gel floss is sheared between the inner contacting surfaces of the teeth, and finally, the elongated wedged of gel floss is pulled upwards and out between the surfaces of the teeth. The forces encountered in the act of flossing are: tension, shearing, tearing under extreme tension.

This invention advances the flossing art by providing strong, soft, and extreme tear resistant invention gels made from multiblock copolymers which invention gels are substantially as soft as the gums surrounding the teeth.

The invention gels can also be formed directly into articles or remelted in any suitable hot melt applicator and extruded into shaped articles and films or spun into threads, strips, bands, yarns, or other shapes using a tubing header, multi-strand header, wire coating header, and the like With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity·(5806×103)(th)(w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of *ENCYCLOPEDIA OF POLYMER SCIENCE AND ENGINEERING,* 1987 which volumes are incorporated herein by reference.

The invention gels is excellent for cast molding and the molded products have various excellent characteristics which cannot be anticipated form the properties of the raw components. Other conventional methods of forming the composition can be utilized.

The high viscosity SEEPS type block copolymers with -E- midblock can achieve improvements in one or more physical properties including improved damage tolerance, improved crack propagation resistance, improved tear resistance, improved resistance to fatigue of the bulk gel and resistance to catastrophic fatigue failure of gel composites, such as between the surfaces of the gel and substrate or at the interfaces of the interlocking material(s) and gel, which improvements are not found in amorphous gels at corresponding gel rigidities.

As an example, when fabric interlocked or saturated with amorphous S-EB-S gels (gel composites) are used as gel liners for lower limb or above the knee prosthesis to reduce pain over pressure areas and give relief to the amputee, the commonly used amorphous gels forming the liners can tear or rip apart during marathon racewalk after 50–70 miles. In extended use, the amorphous gels can rip on the bottom of the liner in normal racewalk training of 40–60 miles over a six weeks period. In such demanding applications, the invention gels are especially advantageous and is found to have greater tear resistance and resistance to fatigue resulting from a large number of deformation cycles than amorphous gels. The invention gels are also useful for forming various orthotics and prosthetic articles such as for lower extremity prosthesis of the L5664 (lower extremity socket insert above knee), L5665 (socket insert, multi-durometer, below knee), L5666 (below knee, cuff suspension interface), L5667 (below knee, above knee, socket insert, suction suspension with locking mechanism) type devices as described by the American Orthotic & Prosthetic Association (AOPA) codes. The invention gels are useful for making AOPA code devices for upper extremity prosthetics. The devices can be cast molded or injection molded in combination with or without fiber or fabric backing or fiber or fabric reinforcement. When such liners are made without fabric backing, various invention gels can be used to form gel-gel and gel-gel-gel composites and the like with varying gel rigidities for the different gel layer(s).

Health care devices such as face masks for treatment of sleep disorder require non tacky invention gel. The gel forming a gel overlap portion on the face cup at its edge conforming to the face and serve to provide comfort and maintain partial air or oxygen pressure when worn on the face during sleep. Although tacky gels can be made from the invention gel, tacky gels because of its tactile feel are undesirable for such applications as face masks and other prolong skin contact uses.

The invention gel can be formed into gel strands, gel bands, gel tapes, gel sheets, and other articles of manufacture in combination with or without other substrates or materials such as natural or synthetic fibers, multifibers, fabrics, films and the like. Moreover, because of their improved tear resistance and resistance to fatigue, the invention gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the invention gels are more tear resistant, they are especially useful for making condoms, toy balloons, and surgical and examination gloves. As toy balloons, the invention gels are safer because it will not rupture or explode when punctured as would latex balloons which often times cause injures or death to children by choking from pieces of latex rubber. The invention gels are advantageously useful for making gloves, thin gloves for surgery and examination and thicker gloves for vibration damping which prevents damage to blood capillaries in the fingers and hand caused by handling strong shock and vibrating equipment. Various other gel articles can be made from the advantageously tear resistant invention gels and invention gel composites of the inventions include gel suction sockets, suspension belts.

The invention gels are also useful for forming orthotics and prosthetic articles such as for lower extremity prosthesis described below. Porous, webbing or matting that are skin breathe-able comprising the gel strands can be formed into a webs or matting by cold forming sandwiched gel strand-composites using alkyl cyanoacrylates such as ethyl, butyl, methyl, propyl cyanoacrylates and the like. The alkyl cyanoacrylates (AC) will interlock with the soft gelatinous elastomer composition of the invention, thereby resulting in gel-(AC)-gel composite webbing or matting articles. Alkyl cyanoacrylates are useful for interlocking gel of the invention with other substrates such as pottery, porcelain, wood, metal, plastics, such as acrylics, ABS, EPDM, nylon Fiberglass, phenoics, plexiglass, polycarbonate, polyesters, polystyrene, PVC, urethanes and the like. Other cyanoacrylates such as cyanoacrylate ester are inhibited and do not interlock with the invention gels.

In applications where extreme tear resistance, low rigidity, high elongation, good compression set and excellent tensile strength are important, the invention gels would be advantageous. The invention gels can be formed into any desired shaped, size and thickness suitable as a cushion; the shaped composition can be additionally surrounded with film, fabric, foam, or any other desired material or combinations thereof. The original shape can be deformed into another shape (to contact a regular or irregular surface) by pressure and upon removal of the applied pressure, the composition in the deformed shape will recover back to its original shape. A cushion can be made by forming the composition into a selected shape matching the contours of the specific body part or body region. Moreover, the composition can be casted onto such materials, provided such materials substantially maintain their integrity (shape, appearance, texture, etc.) during the casting process. The same applies for brace cushions for the hand, wrist, finger, forearm, knee, leg, etc.

Other uses include: shaped articles as toys, optical uses (e.g cladding for cushioning optical fibers from bending stresses) and various optical devices, as lint removers, dental floss, as tips for swabs, as soft elastic fishing baits, as a high vacuum seal (against atmosphere pressure) which contains a useful amount of a mineral oil-based magnetic fluid particles, in the form of (casted, extruded, or spun formed) threads, strips, yarns, strands, tapes which can be weaved into cloths, fine or coarse fabrics. Still other uses include: games; novelty, or souvenir items; elastomeric lenses, light conducing articles, optical fiber connectors; athletic and sports equipment and articles; medical equipment and articles including derma use and for the examination of or use in normal or natural body orifices, health care articles; artist materials and models, special effects; articles designed for individual personal care, including occupational therapy, psychiatric, orthopedic, podiatric, prosthetic, orthodontic and dental care; apparel or other items for wear by and on individuals including insulating gels of the cold weather wear such as boots, face mask, gloves, full body wear, and the like have as an essential, direct contact with the skin of the body capable of substantially preventing, controlling or selectively facilitating the production of moisture from selected parts of the skin of the body such as the forehead, neck, foot, underarm, etc; cushions, bedding, pillows, paddings and bandages for comfort or to prevent personal injury to persons or animals; housewares and luggage; vehicle impact deployable air bag cushions; medical derma use and for the medical examination through surgical orifices of the human body, health care articles, artist materials and models, special effects, articles designed for individual personal care, including occupational therapy, psychiatric, orthopedic, podiatric, prosthetic, orthodontic and dental care, apparel or other items for wear by and on individuals including insulating invention gels of the cold weather wear such as boots, face mask, gloves, full body wear in direct contact with the skin of the body capable of substantially preventing, controlling or selectively facilitating the production of moisture from selected parts of the skin of the body such as the forehead, neck, foot, underarm, etc; cushions, bedding, pillows, paddings and bandages for comfort or to prevent personal injury to persons or animals, as articles useful in telecommunication, electrical utility, industrial and food processing, in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components, as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes.

The gel articles molded from the instant compositions have various additional important advantages in that they do not crack, creep, tear, crack, or rupture in flexural, tension, compression, or other deforming conditions of normal use, but rather the molded articles made from the instant composition possess the intrinsic properties of elastic memory enabling the articles to recover and retain its original molded shape after many extreme deformation cycles.

The instant compositions can be formed in any shape; the original shape can be deformed into another shape (to contact a regular or irregular surface) by pressure and upon removal of the applied pressure, the composition in the deformed shape will recover back to its original shape.

The invention gels can be made into useful gel articles having no need for a protective covering, but a protective covering may be use as required. Such interlocking with many different materials produce gel composites having many additional uses. The high tear resistant soft invention gels are advantageously suitable for a safer impact deployable air bag cushions.

The invention gels are especially suitable and have uses where resistance to dynamic stretching, shearing and tearing forces are particularly useful such as those forces acting during fishing as described above and as dental flossing. In the case of dental flossing, freeze dried dental paste can also be incorporated into the gel and formed into dental floss by passing coating the dental floss surface with flavors or other agents. Not only is the dental floss a floss, it is an effective tooth brush in between the tooth gap between making it a floss-brush with activated tooth past build in. The gel compounded with toothpaste can contain any anticavity agents including sodium fluoride, any antigingivitis agents, any whitening agents, and any plaque fighting agents. Freeze dry or powders containing hydrated silica, sorbitol, PVM/MA copolymer, sodium lauryl sulfate, flavor, sodium hydroxide, triclosan, monoammonium phosphate, calcium sulfate, ammonium chloride, magnesium chloride, methylparaben, propylparaben, coloring, and the like can be compounding into the gel composition forming a floss-brush gel composition.

Gel floss formed from the invention gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft gel floss with softness substantially matching the softness of the gums are of great advantage for use by children and for flossing teeth surrounded by sensitive and tender gums.

The shear resistant characteristics of the invention gels can be indirectly determined by subjecting the gel to the shear forces of a pair of twisting strings and the resulting inward pulling forces of the twisting strings can be directly read off of a spring scale. As a pair of strings are gradually twisted, typical values will range from less than one pound to fifty pounds and greater. As the string is being twisted (simulating increased shearing forces), the measured pulling forces can range from a low value of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . to values of 40, 50, 60, 70, 80 pounds and greater.

Gel material of low strength can not resist the tremendous shearing action of the twisting strings. The twisting action of the strings can exhibit a first order twist, a second order twist, or higher order twists. A first order twist refers to one or more twists of a pair of strings (i.e. a pair of strings when twisted together forms a small tight binding helix). A second order twist refers to one or more large binding helixes build up by a pair of strings that have been twisted beyond the maximum number of twist which normally produce small tight binding helixes of the first order kind. Similarly, a third order twist refers to a much larger tightly binding helix build up by the maximum number of second order twists produced by the pair of twisting strings. The third order twist may be manifested by the appearance of a branch of two or more twist of the first order twisting strings.

The order of twisting will increase (from a one, two, three, and higher order twist) until the rubber band breaks. Likewise, a looped string with one end attached to a spring scale and the other end attached to a fixed anchor can be twisted into a first, second, third, and higher ordered twist state. This method can be utilized to directly measure the force generated for each ordered twist states. The static force generated by twisting a string on a spring scale is a way of determining the shear force generated in the shearing action of forcing the gel floss between two closely contacting teeth when flossing.

In considering dental flossing criteria, one or more of the following conditions can be regarded as critical factors for dental flossing gels.

Shear Resistant Criteria

For the invention gels to be considered useful for flossing, the invention gels, critically, should withstand a twisting string shearing force of at least about 5 Kg, more advantageously at least about 8 Kg, and still more advantageously at least about 10 Kg of inward pulling force of a pair of twisting strings measured directly on a spring scale.

Flossing Cycle Criteria

For the invention gels to be considered useful for flossing, the invention gels, critically, should advantageously be able to perform at least 4 flossing cycles, more advantageously 8 cycles, and still more advantageously of about 20 cycles without breaking apart when a 3.0 mm diameter gel strand is tested on a set of simulated upper front teeth fully contacting under a uniform spring load of (0.9027 Kg) two pounds. The simulated upper front teeth comprises two small stainless steel rollers (⅜" dia.) facing lengthwise parallel and forced together so as to form a contact length of ½ inches under a spring load of two pounds as measured by a Entran® model ELO-200-4 load cell adjusted by a straight micrometer at room temperature.

Gel Strength Criteria

For the invention gels to be considered useful for flossing, the invention gels, critically, should advantageously exhibit a tensile strength of at least 5 Kg/cm$^2$ (when extended to break as measured at 180° U bend around a 5.0 mm mandrel attached to a spring scale) and more advantageously at least 8 Kg/cm$^2$, and still more advantageously of about 10 Kg/cm$^2$ and higher. The invention gels useful as dental floss can exhibit tensile strengths at break of at least 20 Kg/cm$^2$, more advantageously of at least 40 Kg/cm$^2$, and exceptionally more advantageously at least 60 Kg/cm$^2$. Typically, the tensile strengths range from about 20 Kg/cm$^2$ to about 110 Kg/cm2 and higher, more typically from about 30 Kg/cm$^2$ to 80 Kg/cm$^2$ and higher, especially more typically from about 40 Kg/cm$^2$ to about 90 Kg/cm$^2$ and higher, and exceptionally typically from about 50 Kg/cm$^2$ to about 100 Kg/cm$^2$ and higher.

Propagatine Tear Criteria

As a minimum, for the Invention gels to be considered useful for flossing, the invention gels, critically, should advantageously exhibit a propagating tear force (when propagating a tear as measured at 180° U bend around a 5.0 mm diameter mandrel attached to a spring scale) of at least about 1 Kg/cm, more advantageously at least 2 Kg/cm, and still more advantageously of about 3 Kg/cm and higher. The invention gels useful as dental floss can exhibit tear strengths of at least 4 Kg/cm and higher, more advantageously of at least 6 Kg/cm and higher, exceptionally more advantageously of at least 8 Kg/cm and higher. Typically, the tear propagation strength can range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For the Invention gels to be considered useful for flossing, the invention gels, critically, should advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. The extreme tear resistant invention gels typically will exhibit even higher tension tear values.

Rigidity Criteria

The rigidities of the extreme tear resistant useful for flossing can advantageously range from about 350 gram to about 1,800 gram Bloom, more advantageously from about 400 gram to about 1,500 gram Bloom, especially more advantageously from about 450 gram to about 1,200 gram Bloom, still more advantageously from about 450 gram to about 1,000 gram Bloom, and less advantageously at values of greater than 1,800 gram Bloom.

In general, as a minimum, the flossing invention gels should exhibit several critical properties, including advantageously the ability to: (1) withstand a shearing force of at least about 5 Kg under the string twisting test described above, (2) perform at least 4 flossing cycles without breaking apart when tested on a set of simulated upper front teeth fully contacting under a uniform spring load of two pound, (3) exhibit a tensile strength of at least 5 Kg/cm$^2$ and higher, (4) exhibit a propagating tear force at 180° U bend tear test of at least about 1 Kg/cm, and (5) exhibit a propagating tension tear force (on a notched cylindrical sample) of at least about 1 Kg/cm.

For use as a dental floss, the gel is made (by extruding, spinning, casting, etc) as a continuous gel strand, the gel strand can be in the shape of a fiber of a selected diameter (from less than about 0.15 to about 5.0 mm and greater) as a continuous tape having a selected width and thickness (less than 0.10 mm thin to about 5.0 mm and thicker) or in any desired shape suitable for flossing. The fiber, tape or a selected shape is then cut to a desired length, rolled up and placed into a dispenser suitable for containing and dispensing a measured use amount of gel floss. The continuous fiber and tape can be partly cut or notched for measured single or multiple use. When the floss is pulled from the dispenser to a point showing the notched or cut mark on the length of gel floss, the lid is pushed down on the gel floss nipping it and allowing the floss to be further pulled and separated at the notched or cut point. Additionally, a suitable floss dispenser containing a measured length of gel floss can be fitted with a cutting edge attached to its lid or on its body and the uncut and un-notched gel floss can be dispensed from the dispensing container and cut at the desired measured use length by pressing close the dispenser cutting edge down on the floss so as to nip and cut the gel or by simply closing the dispenser lid or running the gel along the cutting edge on the dispenser body separating a useful length of gel floss.

In practice, typically during flossing, a gel strand will under go various deformations, some of these deformations can be measured, including original shape, extended shape under tension, nipping force, and nipped deformation under a measured force and width. Typically, any shaped gel strand can be used for flossing, a square cross-section, a circular cross-section, a rectangular cross-section, round, oval, etc. For example, a 2.35 mm diameter strand when extended under a force of 2.5 kg can be nipped down to 0.14 mm thickness (along a 3 mm uniform width of its cross-section) by a force of 0.9072 Kg (2.0 pound force), a reduction of 16.78:1, a 1.89 mm diameter strand when extended under a force of 2.5 kg can be nipped down to 0.14 mm thickness by a force of 0.9072 Kg (2.0 pound force), a reduction of 13.5:1; a 2.75 mm diameter strand when extended under a force of 2.5 kg can be nipped down to 0.19 mm thickness by a force of 0.9072 Kg (2.0 pound force), a reduction of 14.4:1; and a 2.63 mm diameter strand when extended under a force of 2.5 kg can be nipped down to 0.19 mm thickness by a force of 0.9072 Kg (2.0 pound force), a reduction of 13.8:1. the cross-section of the gel floss can be reduced to any degree by stretching and nipping (from less than about 1% to about 1,600% and higher). Advantageously, a gel having the required strength, tear resistance, gel rigidity, and other characteristics described can be formed into a floss of any selected cross-section and thickness provided the floss is capable of being stretched when flossing under tension without breaking. Typically the stretching or pulling force is from about less than 0.1 Kg to about 3 Kg and higher. The cross-section of the strand of gel floss should be capable of being nipped by a 0.9027 Kg (2 pounds) force applied across a width of 3 mm from its original cross-sectional dimensions to a nipped thickness of about 3.0 mm to about 0.02 mm and lower, more advantageously from about 2.5 mm to about 0.04 mm and lower, still more advantageously from about 2.0 mm to about 0.08 mm and lower; especially advantageously from about 1.5 mm to about 0.15 mm and lower; especially more advantageously from about 1.2 mm to about 0.20 mm and lower; especially still more advantageously from about 10 mm to about 0.25 mm and lower.

The invention gels made from higher viscosity copolymers (I) are resistant to breaking when sheared than triblock copolymer gels. This can be demonstrated by forming a very soft gel, for example 100 parts copolymer to 800 parts plasticizing oil. The soft gel is cut into a strip of 2.5 cm×2.5 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the copolymer (I) invention gels will not easily break completely apart as would gels formed from triblock copolymers. In some cases, it will take two, three, or more attempts to shear a high viscosity copolymer (I) gel strip this way. Whereas, a lower viscosity triblock copolymer gel strip can be sheared apart on the first try. For gels made from copolymers with viscosities of 5 wt % solution in Toluene, their shear resistance will decrease with decreasing viscosity. For example, the shear strengths as tested by hand shearing described above of invention gels made from copolymers having polymer viscosities of 150, 120, 110, 105, 95, 90, 89, 85, 70, 60, 58, 48, 42, 40, 35, 28, 27, 25, 21 cps, and the like can be expected to decrease with decreasing viscosity.

The tensile strengths of multiblock copolymer invention gels made from higher viscosity copolymers (I) can be slightly lower than or equal to the tensile strengths of gels made from lower solution viscosity triblock copolymers (III).

Strands of invention gels comprising higher viscosity multiblock copolymers will perform better than gel strands made from gels of lower viscosity triblock copolymers when used in flossing amalgam molars and more than three times better when used in flossing front teeth.

Invention gels, in general, will exhibit higher tensile and greater tear resistance than their parent invention gels containing higher concentrations of plasticizer. As compared to spongy nylon, regular waxed nylon, and extra fine unwaxed nylon when flossing amalgam molars, the performance of multiblock copolymer invention gels are on the average substantially better.

While advantageous components and formulation ranges based on the desired properties of the multiblock copolymer invention gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

The gels of the invention can be use for making air bags. The expansion of the gel air bag is substantially pure volume expansion or dilation as related to K, bulk modulus, y, young's modulus: $K=y/3(1-2t)$, $t=3k-2n/6k-2n$, where t=poisson's ratio, $b=1/k$ compressibility=−change in V/(V·change in pressure P).

Surface expansion measure of air bag from initial to expanded state is from 630 to 833% depending on thickness of original air bag. The initial air bag thickness can vary from 0.5 cm to 10 cms. (0.5, 1, 2, 3, 4, 5, 6, 7, 8, 9, 10 cm and higher).

While advantageous components and formulation ranges based on the desired properties of the gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

EXAMPLE I

Gels of 100 parts of Kraton G1651, Kraton RP-6917 (amorphous S-EB-S), Septon 8006 (amorphous S-EB-S), Kraton RP-6918, Septon S2006 (amorphous S-EP-S) and a high viscosity radial amorphous midblock segment (SEB)n triblock copolymers and 1,600, 1,200, 1,000, 800, 600, 500, 450, 300, 250 parts by weight of Duraprime 200 white oil (plasticizer having Vis. cSt @40° C. of 39.0) are melt blended, test, and tack probe samples molded, the bulk gel rigidities are found to be within the range of 2 to 1,800 gram Bloom and the tensile strength, notched tear strength, and resistance to fatigue are found to decrease with increase amounts of plasticizers, while tackiness of the gels is found to be greater than 7.6 gram Tack.

EXAMPLE II

Gels of 100 parts of Septon polyethylene containing (SEEPS) copolymers 4033, 4055, and 4077 and 1,600, 1,200, 1,000, 800, 600, 500, 450, 300, 250 parts by weight of Duraprime 200 white oil (plasticizer having Vis. cSt@40° C. of 39.0) are melt blended, test and tack probe samples molded, the bulk gel rigidities are found to be within the range of 2 to 1,800 gram Bloom and the gel tackiness are found to increase with increase amounts of plasticizers and the tack greater than 7.6 gram Tack.

EXAMPLE III

Gels of 100 parts of Septon polyethylene containing (SEEPS) copolymers 4033, 4055, and 4077 in combination with sufficient amounts of a Dow S series poly(ethylene/ styrene) random copolymer (250,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE IV

Gels of 100 parts of Septon 4045 (polyethylene containing S-E/EP-S having a styrene content of 37.6) and 1,600, 1,200, 1,000, 800, 600, 500, 450, 300, 250 parts by weight of Duraprime Klearol white oil (plasticizer having Vis. CSt @40° C. of 7–10) are melt blended, test and probe samples molded, the bulk gel rigidities are found to be within the range of 2 to 2,000 gram Bloom and the tackiness is found to be less than about 1 gram Tack.

EXAMPLE V

Gels of 100 parts of Septon polyethylene containing (SEEPS) copolymers 4033, 4055, and 4077 in combination with sufficient amounts of Septon 2104 (Amorphous SEPS having a high styrene content of 65) and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and tack is found to decrease with decreasing plasticizer content and in all instances substantially lower than the gels of Example I and II.

EXAMPLE VI

Gels of 100 parts of Septon polyethylene containing (SEEPS) copolymers 4033, 4055, and 4077 in combination with sufficient amounts of a Dow M series poly(ethylene/styrene) random copolymer (350,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE VII

Gels of 100 parts of Septon polyethylene containing (SEEPS) copolymers 4033, 4055, and 4077 in combination with sufficient amounts of a Dow E series poly(ethylene/styrene) random copolymer (240,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE VIII

Gels of 100 parts of Septon polyethylene containing (SEEPS) copolymers 4033, 4055, and 4077 in combination with polystyrene homopolymers (having Mw of 3,000; 4,000; 5,000; 6,000, 7,000; 8,000; 9,000; 10,000; 11,000; 12,000, 13,000; 14,000; 15,000; 16,000; 17,000; 18,000; 19,000; 20,000; 30,000; 40,000; 50,000; 60,000; 70,000; 80,000; 90,000) in sufficient amounts to form gel blends with total styrene content of 37, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis CSt @40° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than the gels of Example I and II.

EXAMPLE IX

Gels of 100 parts of Septon polyethylene containing (SEEPS) copolymers 4033, 4055, and 4077 in combination with sufficient amounts of a Dow M series poly(ethylene/styrene) random copolymer (350,000 Mw) having a high styrene content sufficient to form gel blends with total styrene contents of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE X

Gels of 100 parts of Septon polyethylene containing (SEEPS) copolymers 4033, 4055, and 4077 in combination with sufficient amounts of a Dow S series poly(ethylene/styrene) random copolymers (with Mw of 140,000; 250,000 and 340,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XI

Gels of 100 parts of Septon polyethylene containing (SEEPS) copolymers 4033, 4055, and 4077 in combination with sufficient amounts of a Dow E series poly(ethylene/styrene) random copolymers (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XII

Gels of 100 parts of Septon polyethylene containing (SEEPS) copolymers 4033, 4055, and 4077 in combination with sufficient amounts of a Dow M series poly(ethylene/styrene) random copolymer (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XIII

Gels of 100 parts of Dow E series polyethylene containing poly(ethylene/styrene) random copolymer (with Mw of 250,000; 340,000 and 400,000) having a high styrene content sufficient to form gel blends with total styrene content of 37, 40, 45, 48, 50, 55, and 60 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, test, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XIV

Gels of 100 parts of Septon polyethylene containing (SEEPS) copolymers 4033, 4055, and 4077 in combination with polystyrene (of 2,500 Mw, 4,000 Mw, 13,000 Mw, 20,000 Mw, 35,000 Mw, 50,000 Mw, and 90,000 Mw; poly(alpha-methylstyrene) (of 1,300 Mw, 4,000 Mw; poly(4-methylstyrene)(of 72,000 Mw), Endex 155, 160, Kristalex 120, and 140) in sufficient amounts to form gel blends with total styrene content of 37, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than the gels of Example I and II.

EXAMPLE XV

Examples XIV is repeated and gels of 100 parts of (S-EB$_{45}$-EP-S), (S-E-EB$_{25}$-S), (S-EP-E-EP-S), (S-E-EB-S), (S-E-EP-S), (S-E-EP-E-S), (S-E-EP-EB-S), (S-E-EP-E-EP-S), (S-E-EP-E-EB-S), (S-E-EP-E-EP-E-S), (S-E-EP-E-EB-S), (S-E-EP-E-EP-EB-S), and (S-E-EP-E-EP-E-S) block copolymers are each melt blended, tests and probe samples molded, the bulk gel rigidities are found to be within the range of 2 to 1,800 gram Bloom and tack is found to decrease with decreasing plasticizer content and in all instances substantially lower than the gels of Example I and II.

EXAMPLE XVI

Example XIV is repeated and minor amounts of 2, 5, 10 and 15 parts of the following polymers are formulated with each of the triblock copolymers: styrene-butadiene-styrene block copolymers, styrene-isoprene-styrene block copolymers, low viscosity styrene-ethylene-butylene-styrene block copolymers, styrene-ethylene-propylene block copolymers, styrene-ethylene-propylene-styrene block copolymers, styrene-butadiene, styrene-isoprene, polyethyleneoxide, poly(dimethylphenylene oxide), polystyrene, polybutylene, polyethylene, polypropylene, high ethylene content EPDM, amorphous copolymers based on 2,2-bistrifluoromethyl-4,5-difuoro-1,3-dioxole/tetrafluoroethylene. The bulk gel rigidities of each of the formulations are found to be within the range of 2 gram to 2,000 gram Bloom and tack is found to decrease with decreasing plasticizer content and in all instances substantially lower than the gels of Example I and II.

EXAMPLE XVII

Molten gels of Examples III–XVI are formed into composites with paper, foam, plastic, elastomers, fabric, metal, concrete, wood, glass, ceramics, synthetic resin, synthetic fibers, and refractory materials and the resistance to fatigue of the composite-gels at corresponding rigidities are found to be greater than that of the composite-amorphous gels of Example I.

EXAMPLE XVIII

Three cm thick sheets of each of the gels of Example XIV and the amorphous gels of Example I are tested by repeatedly displacing the sheets to a depth of 1 cm using a 10 cm diameter smooth (water soaked) wood plunger for 1,000, 5,000, 10,000, 25,000, 50,000, and 100,000 cycles. The sheets of gels are found capable of exhibiting greater fatigue resistance than the sheets of amorphous gels at corresponding rigidities.

EXAMPLE XIX

Gels of 100 parts of Septon polyethylene containing (SEEPS) copolymers 4033, 4055, and 4077 in combination with sufficient amounts of a Dow poly(ethylene/styrene) random copolymers ES16 having 37.5% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XX

Gels of 100 parts of Septon polyethylene containing (SEEPS) copolymers 4033, 4055, and 4077 in combination with sufficient amounts of a Dow poly(ethylene/styrene) random copolymers ES24 having 26.6% crystallinity and 800, 600, 500, 450, 300, 250 parts by weight of Duraprime 55, 70, Klearol, Carnation, Blandol, Benol, Semtol 85, 70, and 40 (plasticizers having Vis CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXI

Gels of 100 parts of Septon polyethylene containing (SEEPS) copolymers 4033, 4055, and 4077 in combination with sufficient amounts of a Dow poly(ethylene/styrene) random copolymers ES27 having 17.4% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXII

Gels of 100 parts of Septon polyethylene containing (SEEPS) copolymers 4033, 4055, and 4077 in combination with sufficient amounts of a Dow poly(ethylene/styrene) random copolymers ES28 having 22.9% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXIII

Gels of 100 parts of Septon polyethylene containing (SEEPS) copolymers 4033, 4055, and 4077 in combination with sufficient amounts of a Dow poly(ethylene/styrene) random copolymers ES30 having 19 6% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXIV

Gels of 100 parts of Septon polyethylene containing (SEEPS) copolymers 4033, 4055, and 4077 in combination with sufficient amounts of a Dow poly(ethylene/styrene) random copolymers ES44 having 5.0% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXV

Gels of 100 parts of Septon polyethylene containing (SEEPS) copolymers 4033, 4055, and 4077 in combination with sufficient amounts of a Dow poly(ethylene/styrene) random copolymers ES72 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVI

Gels of 100 parts of Septon polyethylene containing (SEEPS) copolymers 4033, 4055, and 4077 in combination with sufficient amounts of a Dow poly(ethylene/styrene) random copolymers ES73 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVII

Gels of 100 parts of Septon polyethylene containing (SEEPS) copolymers 4033, 4055, and 4077 in combination with sufficient amounts of a Dow poly(ethylene/styrene) random copolymers ES74 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVIII

Gels of 100 parts of Septon polyethylene containing (SEEPS) copolymers 4033, 4055, and 4077 in combination with sufficient amounts of a Dow poly(ethylene/styrene) random copolymers ES69 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXIX

Gels of 100 parts of Septon polyethylene containing (SEEPS) copolymers 4033, 4055, and 4077 in combination with sufficient amounts of a Dow poly(ethylene/styrene) random copolymers ES62 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXX

Gels of 100 parts of Septon (SEPS) copolymers Kraton GRP6918 in combination with each of a Dow poly(ethylene/styrene) random copolymers ES16, ES24, ES27, ES28, ES30, and E544 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXI

Gels of 100 parts of Septon (SEBS) copolymers S8006 and Kraton G1651, G1654 in combination with sufficient amounts of a Dow poly(ethylene/styrene) random copolymers ES16, ES24, ES27, ES28, ES30, and ES44 and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities arc found to be within the range of 2 gram to 1,800 gram Bloom and the notched tear strength and resistance to fatigue of the gel at corresponding rigidities are found to be greater than that of amorphous gels of Example I.

EXAMPLE XXXII

Gels of 100 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035) and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXIII

Gels of 100 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035) and 800, 600, 500, 450, 300, 250 parts by weight of Duraprime 55, 70, Klearol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXIV

A 15 layer rolled/folded gel film actuator having a active muscle length of 10 mm and a diameter of 3 mm (made from 0.5 mm thick Septon 4055, 4077, 4045 SEEPS having a 500, 600, 700, 800, 1200, 1600, 1800, 2000, 2300, 2500 gram Bloom gel) is found to have a stroke and a force greater than actuators made from amorphous SEPS, SEBS gels.

EXAMPLE XXXV

A 15 layer rolled/folded gel film actuator having a active muscle length of 10 mm and a diameter of 3 mm (made from 0.5 mm thick Ethylene-styrene copolymers: ES16, ES24, ES27, ES28, ES28, and ES30 having a 500, 600, 700, 800, 1200, 1600, 1800, 2000, 2300, 2500 gram Bloom gel) is found to have a stroke and a force greater than actuators made from amorphous SEPS, SEBS gels.

EXAMPLE XXXVI

A 15 layer rolled/folded gel film actuator having a active muscle length of 10 mm and a diameter of 3 mm (made from 0.5 mm thick made from a 50% of Ethylene-styrene copolymers: ES16, ES24, ES27, ES28, ES28, ES30 with a 50% of Septon 4055 having a 500, 600, 700, 800, 1200, 1600, 1800, 2000, 2300, 2500 gram Bloom gel) is found to have a stroke and a force greater than actuators made from amorphous SEPS, SEBS gels.

EXAMPLE XXXVI

Unexpanded methacrylonitrile microspheres #051, #053, #091, #091-80, and #092-120 precompounded in masterbatches in the shape of rods, strands, ropes are configured in 3-D form and expanded in place with hot gel made from Duraprime 55 white oil in varying amounts to yield oil/microsphere mixtures having the following approximate viscosities (poise): 0.5, 0.8, 1.5, 18, 34, 100, 150, 250, 400, 460, 480, 560, 720, 1000, and 2000.

EXAMPLE XXXVI

Unexpanded methacrylonitrile microspheres #051, #053, #091, #091-80, and #092-120 precompounded in masterbatches in the shape of fibers, hairs, ficrofibers, threads, are configured in 3-D form and expanded in place with hot gel made from Duraprime 70 white oil in varying amounts to yield oil/microsphere mixtures having the following approximate viscosities (poise): 0.5, 0.8, 1.5, 18, 34, 100, 150, 250, 400, 460, 480, 560, 720, 1000, and 2000.

EXAMPLE XXXVI

Unexpanded methacrylonitrile microspheres #051, #053, #091, #091-80, and #092-120 precompounded in masterbatches in the shape of solid sphere, rod, cone, regular and irregular shapes are configured in 3-D form and expanded in place with hot gel made from Duraprime 90 white oil in varying amounts to yield oil/microsphere mixtures having the following approximate viscosities (poise): 0.5, 0.8, 1.5, 18, 34, 100, 150, 250, 400, 460, 480, 560, 720, 1000, and 2000.

EXAMPLE XXXVI

Unexpanded methacrylonitrile microspheres #051, #053, #091, #091-80, and #092-120 precompounded in masterbatches in the shape of sheets are configured in 3-D form and expanded in place with hot gel made from Duraprime 200 white oil in varying amounts to yield oil/microsphere mixtures having the following approximate viscosities (poise): 0.5, 0.8, 1.5, 18, 34, 100, 150, 250, 400, 460, 480, 560, 720, 1000, and 2000.

While preferred components and formulation ranges have been disclosed herein persons of skill in the art can extend these ranges using appropriate material according to the principles discussed herein. Furthermore, Polyethylene containing midblock segment block polymers can be use in blending with other engineering plastics and elastomeric polymers to make alloyed compositions having improved impact and tear resistance properties. All such variations and deviations which rely on the teachings through which the present invention has advanced the art are considered to be within the spirit and scope of the present invention.

What is claimed is:

1. A artificial muscle actuator comprising:
a) one or more thin film layers folded or rolled into the shape of a cylinder forming a center part of said cylinder and an outer part of said cylinder, said film layer having a top surface Mn1 and a bottom surface Mn2, said top surface and said bottom surface each coated with an electrical conducting layer Mc, said conducting layer of said top surface connected by a first electrode on said top surface positioned at said center part and said bottom surface connected by a second electrode on said bottom surface positioned at said outer part; said first and second electrodes being connected to one or more direct current power source or sources, said power supply capable of generating a electrical potential of a positive electrical charge to the first electrode and a negative electrical charge to the second electrode from less than about 100 volt to above about 10,000 volts; said film layers comprising a gel made from one or more copolymers having one or more polyethylene segments and capable of exhibiting crystallinity at about 10° C. and higher as determined by differential scanning calorimetry curve, said gel having rigidities of from less than about 2 gram Bloom to about 1,800 gram Bloom; and said gel being capable of exhibiting greater tear resistance than amorphous gels of poly(styrene-ethylene-propylene-styrene).

2. A artificial muscle actuator comprising:
a) one or more thin film layers folded or rolled into the shape of a cylinder forming a center part of said cylinder and an outer part of said cylinder, said film layer having a top surface and a bottom surface, said top surface and said bottom surface each coated with an electrical conducting layer, said conducting layer of said top surface connected by a first electrode on said top surface positioned at said center part and said bottom surface connected by a second electrode on said bottom surface positioned at said outer part; said first and second electrodes being connected to a direct current power source, said power supply capable of generating a electrical potential of a positive electrical charge to the first electrode and a negative electrical charge to the second electrode of about 100 v, 200 v, 300 v, 400 v, 500 v, 600, 700 v, 800, 900, 1,000 v, 2,000 v, 3,000 v, 4,000 v, 5,000 v, 6,000 v, 7,000 v, 8,000 v, 9,000 v, 10,000 v, 11,000 v, 12,000 v, 15,000 v and higher; said film layers comprising a gel made from one or more copolymers in combination with or without polyphenylene ether, said copolymers having one or more polyethylene segments; and said copolymers capable of exhibiting crystallinity at about 10° C. and higher as determined by differential scanning calorimetry curve, said gel having rigidities of from less than about 2 gram Bloom to about 1,800 gram Bloom; and said gel being capable of exhibiting greater tear resistance than amorphous gels of poly(styrene-ethylene-propylene-styrene).

3. A artificial muscle actuator comprising:
a) one or more thin film layers folded or rolled into the shape of a cylinder forming a center part of said cylinder and an outer part of said cylinder, said film layer having a top surface and a bottom surface, said top surface and said bottom surface each coated with an electrical conducting layer, (E), said conducting layer of said top surface connected by a first electrode on said top surface positioned at said center part and said bottom surface connected by a second electrode on said bottom surface positioned at said outer part; said first and second electrodes being connected to a direct current power source, said power supply capable of generating a electrical potential of a positive electrical charge, to the first electrode and a negative electrical charge, to the second electrode of at least about 10,000 volts; said film layers comprising a composite of one or more gel, G, film layers and one or more electrode, E, coating layers, said composite selected from EGE, EGEGE, EGEGEGE, EGEGEGEGE, and EGEGEGEGEGE; said film layers comprising a gel made from one or more copolymers in combination with or without polyphenylene ether, said copolymers having one or more polyethylene segments; and said copolymers capable of exhibiting crystallinity at about 10° C. and higher as determined by differential scanning calorimetry curve, said gel having rigidities of from less than about 2 gram Bloom to about 1,800 gram Bloom; and said gel being capable of exhibiting greater tear resistance than amorphous gels of poly(styrene-ethylene-propylene-styrene).

* * * * *